(12) United States Patent
Hochareon

(10) Patent No.: US 11,071,845 B2
(45) Date of Patent: Jul. 27, 2021

(54) LOCALIZED THERAPY DELIVERY AND LOCAL ORGAN PROTECTION

(71) Applicant: Nirva Medical, LLC, Vadnais Heights, MN (US)

(72) Inventor: Pramote Hochareon, Vadnais Heights, MN (US)

(73) Assignee: NirvaMed, Inc., Vadnais Heights, MN (US)

( * ) Notice: Subject to any disclaimer, the term of this patent is extended or adjusted under 35 U.S.C. 154(b) by 600 days.

(21) Appl. No.: 15/993,160

(22) Filed: May 30, 2018

(65) Prior Publication Data

US 2018/0272104 A1 Sep. 27, 2018

Related U.S. Application Data

(63) Continuation of application No. 14/721,825, filed on May 26, 2015, now Pat. No. 10,004,874, which is a
(Continued)

(51) Int. Cl.
*A61M 1/36* (2006.01)
*A61M 25/00* (2006.01)
(Continued)

(52) U.S. Cl.
CPC ............ *A61M 25/007* (2013.01); *A61M 1/36* (2013.01); *A61M 1/3604* (2014.02);
(Continued)

(58) Field of Classification Search
CPC .... A61M 1/36; A61M 1/3604; A61M 1/3613; A61M 1/3615; A61M 1/3666;
(Continued)

(56) References Cited

U.S. PATENT DOCUMENTS 4,714,460 A 12/1987 Calderon
4,867,742 A 9/1989 Calderon
(Continued)

OTHER PUBLICATIONS

Search Report dated Feb. 2, 2016 in European Patent Application serial No. 11740297.4.

*Primary Examiner* — Benjamin J Klein

(74) *Attorney, Agent, or Firm* — Haugen Law Firm PLLP

(57) ABSTRACT

A system for perfusing a localized site within a body includes a catheter assembly having a venous access line that is adapted to deliver perfusate to the localized site, a venous or arterial drainage line adapted to drain perfusate from the localized site, and an occlusion device adapted to prevent some or substantially all physiological blood flow between the localized site and the systemic circulation of the body during and in the course of perfusing and draining perfusate to and from the localized site. The system may include a blood circuit associated with the catheter assembly to facilitate blood conditioning for use as the perfusate, in the course of a controlled perfusion and/or drainage of untreated, treated, or inactivated treated blood to and from the localized site. A delivery machine may control the blood circuit and catheter assembly in order to both deliver perfusate to, and drain some or all perfusate from, the localized site in a manner that provides perfusate to substantially only the localized site.

20 Claims, 17 Drawing Sheets

Related U.S. Application Data continuation of application No. 13/576,302, filed as application No. PCT/US2011/023471 on Feb. 2, 2011, now Pat. No. 9,078,980.

(60) Provisional application No. 61/300,703, filed on Feb. 2, 2010.

(51) Int. Cl.
*A61M 5/142* (2006.01)
*A61M 25/10* (2013.01)
*A61M 25/04* (2006.01)

(52) U.S. Cl.
CPC ........ *A61M 1/3613* (2014.02); *A61M 1/3615* (2014.02); *A61M 1/3666* (2013.01); *A61M 5/142* (2013.01); *A61M 25/0071* (2013.01); *A61M 25/10* (2013.01); *A61M 1/369* (2013.01); *A61M 25/04* (2013.01); *A61M 2025/0004* (2013.01); *A61M 2025/0031* (2013.01); *A61M 2025/0037* (2013.01); *A61M 2025/1052* (2013.01); *A61M 2025/1095* (2013.01); *A61M 2205/36* (2013.01)

(58) Field of Classification Search
CPC .... A61M 1/369; A61M 5/142; A61M 25/007; A61M 25/0071; A61M 25/04; A61M 25/10; A61M 2025/0004; A61M 2025/0031; A61M 2025/0037; A61M 2025/1052; A61M 2025/1095
See application file for complete search history.

(56) References Cited

U.S. PATENT DOCUMENTS

| | | |
|---|---|---|
| 5,385,548 A | 1/1995 | Williams et al. |
| 5,411,479 A | 5/1995 | Bodden |
| 5,533,957 A | 7/1996 | Aldea |
| 5,562,606 A | 10/1996 | Huybregts |
| 5,597,377 A | 1/1997 | Aldea |
| 5,794,629 A | 8/1998 | Frazee |
| 5,865,789 A | 2/1999 | Hattler |
| 6,186,146 B1 | 2/2001 | Glickman |
| 6,287,273 B1 * | 9/2001 | Allers ................. A61M 1/3621 604/27 |
| 6,336,910 B1 | 1/2002 | Ohta et al. |
| 6,386,202 B1 | 5/2002 | Frazee |
| 6,626,857 B1 | 9/2003 | Ohta |
| 6,682,499 B2 | 1/2004 | Lenker |
| 6,699,231 B1 * | 3/2004 | Sterman ........... A61B 17/12045 604/509 |
| 6,821,263 B2 | 11/2004 | Lenker |
| 6,896,663 B2 | 5/2005 | Barbut |
| 7,347,810 B2 | 3/2008 | Stamos |
| 2002/0077581 A1 | 6/2002 | Davidner |
| 2002/0128586 A1 | 9/2002 | Barbut |
| 2003/0212304 A1 | 11/2003 | Lattouf |
| 2004/0034272 A1 | 2/2004 | Diaz |
| 2006/0149219 A1 | 7/2006 | Calderon |
| 2006/0149393 A1 | 7/2006 | Calderon |
| 2006/0167398 A1 | 7/2006 | Solar |
| 2006/0258980 A1 | 11/2006 | Bridges |
| 2008/0041516 A1 | 2/2008 | Chiu et al. |

\* cited by examiner

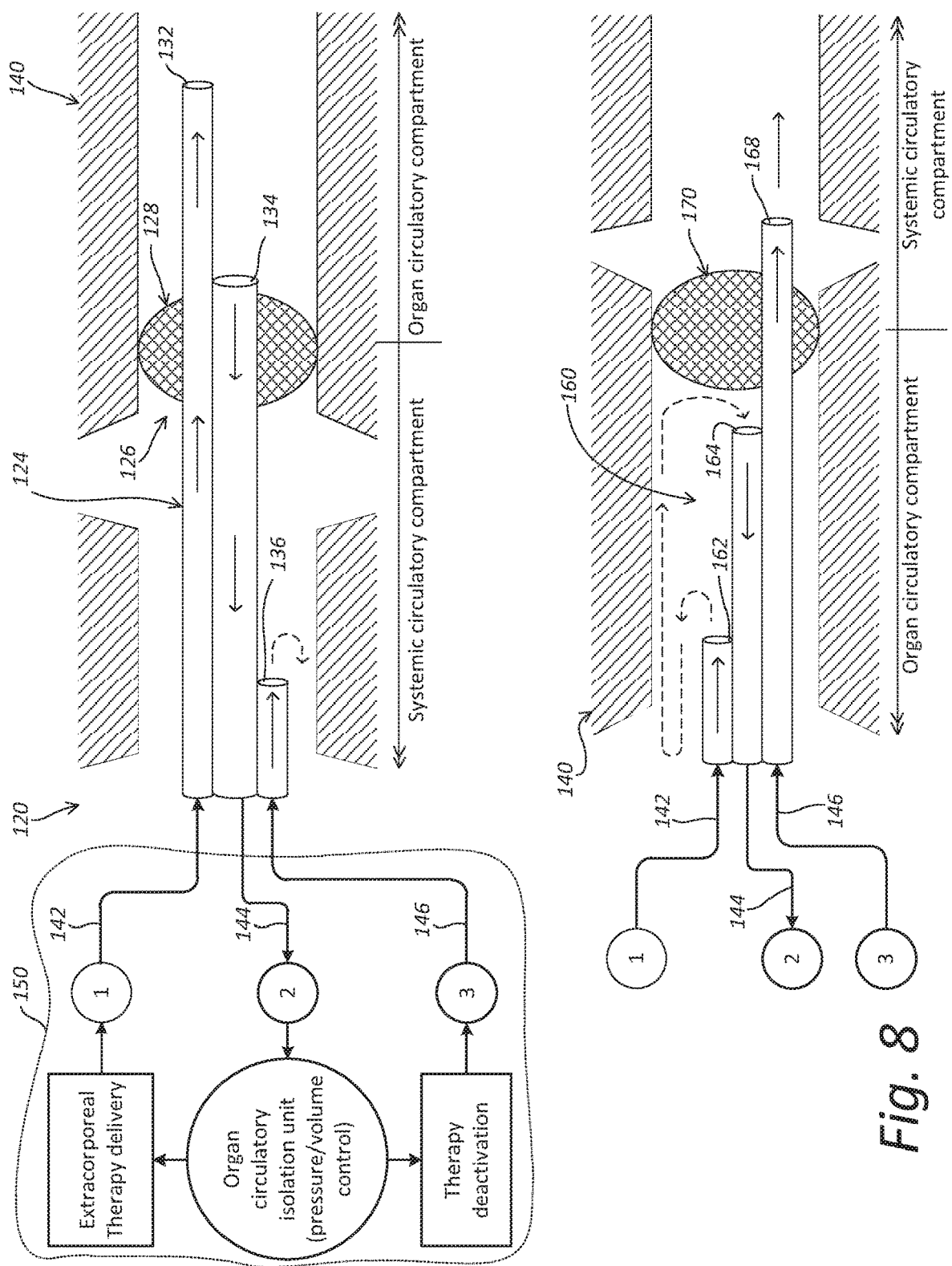

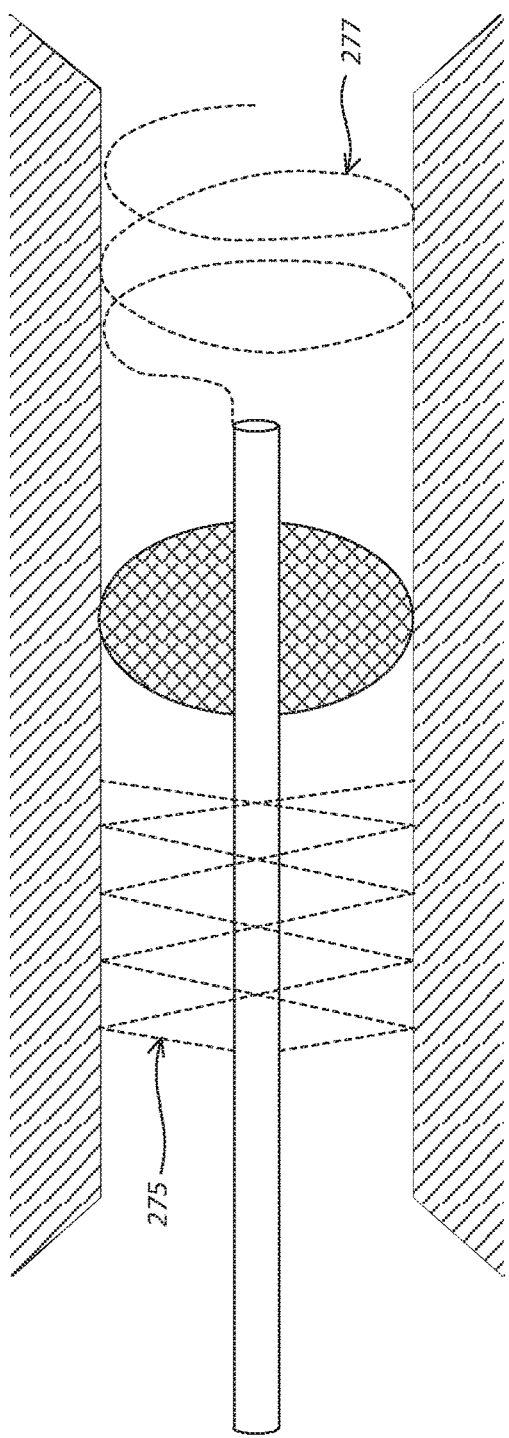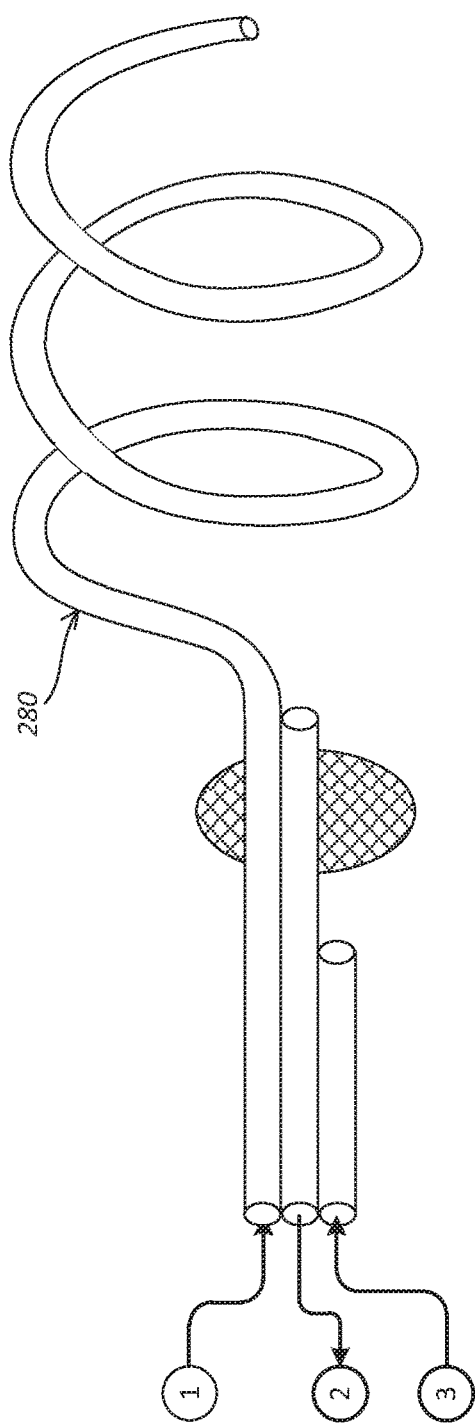
Fig. 13A
Fig. 13B

LOCALIZED THERAPY DELIVERY AND LOCAL ORGAN PROTECTION

CROSS-REFERENCE TO RELATED APPLICATIONS

This application is a continuation of U.S. patent application Ser. No. 14/721,825, filed on May 26, 2015 and entitled "Localized Therapy Delivery and Local Organ Protection", itself a continuation of U.S. patent application Ser. No. 13/576,302, filed on Jul. 31, 2012 and entitled "Localized Therapy Delivery and Local Organ Protection", itself a United States national phase application under 35 U.S.C. § 371 of International Application Serial No. PCT/US11/23471, filed on Feb. 2, 2011 and entitled "Localized Therapy Delivery and Local Organ Protection", which claims priority to U.S. Provisional Application Ser. No. 61/300,703, filed on Feb. 2, 2010, the contents of each of which being incorporated herein in their entirety.

FIELD OF THE INVENTION

The present invention relates to therapy delivery generally, and more particularly to localized delivery of therapy to target body tissue structures, wherein the therapy may be contained at a localized site to minimize or eliminate systemic effect of the therapy.

BACKGROUND OF THE INVENTION

Therapy administration techniques have long relied upon systemic pathways due to the ease of accessibility of such pathways. For example, systemic pathways may be accessed through oral, intravenous, intramuscular, per-cutaneous, sub-dermal, and inhalation delivery techniques. However, most therapies target a specific tissue structure, wherein systemic administrations for such local treatment may be inefficient or ineffective as a result of dilution of the systemic administration and/or undesirable systemic side effects. In either case, maximum benefit of the treatment is not likely realized through systemic administration.

Currently practiced localized administration techniques improve the effectiveness of local treatment by direct application to the target tissue structure. However, dilution of the administered treatment still occurs as a result of systemic blood circulation through the tissue structure. Moreover, convective transport of the applied treatment may also lead to systemic side effects which limit the potential treatment potency, even when administered locally. Consequently, prolonged application of localized, but non-isolated therapy administration does not typically maintain the high organ-to-body concentration gradient needed to provide the maximal effectiveness of the therapy.

Many treatments that show promising results in animal research fail to translate to clinical uses due to intolerable systemic and/or local adverse effects outside the tissue structure targeted for treatment. Such therapies may be aggressive, but crucial treatments for severe or life-threatening conditions. One example is the treatment of a solid tumor, which is typically approached through a systemic intravenous infusion of chemotherapeutic agents to reach the tumor site. Systemic toxicity of many chemotherapeutic agents, however, restricts the ability to maintain a dose rate and/or duration of exposure to effect a response.

Another example is the treatment of ischemic tissue caused by an acute severe disruption in arterial circulation to the damaged tissue. Examples of ischemic injuries are myocardial infarction (heart attack) and cerebrovascular accident (stroke). Treatment of ischemic injury has typically involved a direct arterial intervention. However, conventional arterial intervention techniques require significant time to complete, and introduce risk of secondary injury, such as through arterial emboli and reperfusion injury, which may be caused by a sudden return of blood supply to the tissue after the arterial disruption is resolved.

The current standard treatment for heart attack is reperfusion therapy, primarily by percutaneous coronary intervention (PCI), such as stent and/or balloon angioplasty and/or thrombolytic therapy. The goal of such treatment is to reestablish the tissue perfusion to the myocardium as early as possible in order to minimize tissue damage, and to promote tissue salvage. PCI, however, can cause clot debris to flow downstream and result in a distal occlusion of smaller arteries. Moreover, the return of blood supply to ischemic tissue itself may attack the tissue (i.e. reperfusion injury).

The concept of tissue cooling treatment to prevent or minimize tissue damage caused by arterial circulation disruption and/or reperfusion injury has been explored. However, conventional total-body cooling can cause systemic adverse effects, such as severe shivering, hemodynamic instability due to electrolyte shift and systemic vascular dilation, coagulopathy or increased bleed tendency, and infection, which further complicates patient management. In addition, conventional therapeutic hypothermia administrations may result in ineffective therapy delivery to the target tissue, and is unable to rapidly cool the target issue without the undesired systemic side effects described above. The drawbacks of conventional total-body cooling therefore generally prohibits clinical use of the cooling treatment in both severe ischemic and traumatic injuries, despite evidence in preclinical research demonstrating the effective reduction of tissue death after severe injury with the cooling treatment.

Retrograde therapeutic perfusion, such as perfusion of oxygenated blood delivered retrogradedly to the endangered ischemic myocardium, has been explored as a stand-alone or adjunctive treatment to PCI to cause oxygenated blood to rapidly reach an underperfused myocardium tissue. Retroperfusion of oxygenated blood has also been explored in the context of ischemic brain stroke, in which autologous oxygenated blood may be pumped into one or both of the cerebral venous sinuses through the jugular veins. One conventional method describes occluding both jugular veins by balloon catheters or, alternatively, occluding the drainage paths from higher up in the brain if desired, and continuously pumping arterial blood into one or both of the cerebral sinuses.

In addition to rapidly providing oxygenated blood to ischemic tissue, researchers have realized that venous retroperfusion may provide an advantageous technique for therapeutic hypothermia of retroperfused tissue. Mild hypothermia (32-33° C.) with reperfusion therapy has been shown to provide a significant improvement of tissue protection when compared to reperfusion therapy alone. By directly treating tissue structures with therapeutic cooling, many undesirable side effects of system therapeutic cooling may be avoided.

Despite the promising outcomes of retroperfusion of oxygenated blood, and targeted therapeutic hypothermia through a retroperfusion platform, proposals to date have involved complex systems, including the need for arterial catheterization, and/or inadequate or problematic retroperfusion. Moreover, systems proposed to date fail to substantially isolate the target tissue structure, such that conventional therapy delivery typically results in contamination to the systemic circulation. For various applications, including therapeutic hypothermia, significant contamination is undesired, and limits the effectiveness of the therapy on the targeted tissue structure.

It is therefore an object of the invention to deliver therapy locally, and to isolate the therapy substantially only to the target tissue structure.

It is another object of the invention to maintain a high organ to body therapy gradient, wherein such gradient is the difference between the therapeutic concentration at the target organ versus such therapeutic concentration in the systemic circulation.

SUMMARY OF THE INVENTION

By means of the present invention, organ circulation may be isolated from the systemic circulation so that the organ circulation is compartmentalized from the systemic circulation, while still performing its function for the body. Therapy may therefore be delivered in a manner to maintain either a high organ-to-systemic or systemic-to-organ therapeutic gradient for an extended period of time. In a particular application, the present invention facilitates localized treatment of a specific organ to prevent or minimize systemic side effects. Aggressive treatments that are currently limited or impractical due to the patient's ability to tolerate systemic side effects may potentially be applied through the system of the present invention. Examples of such aggressive treatments include therapeutic hypothermia and chemotherapy. On the other hand, when systemic treatment is preferred, but limited by its toxicity to vital organs, the organ circulatory isolation concept of the present invention may be used to prevent or minimize organ damage from the systemic treatment. Therefore, the ability to localize or isolate aggressive treatments to or from specific organs (tissue structures) can expand the use of certain existing treatments to provide more benefits to more patients.

While several techniques and device configurations are proposed herein, the present concept may be generally described by: (i) localized therapy delivery, (ii) therapy isolation, and (iii) compartmental therapy deactivation. Such principles may be accomplished through a catheterization having an organ perfusion line, an organ drainage line, and a systemic line. As a result, a single catheter platform may serve a variety of clinical applications. In many situations, catheterization with the present system may involve relatively low-risk venous access, and does not require arterial intervention.

BRIEF DESCRIPTION OF THE DRAWINGS

FIG. 7 is a schematic illustration of the system depicted in FIG. 6;

FIG. 8 is a schematic illustration of the system depicted in FIG. 6;

FIG. 13A is an illustration of a balloon fixation device usable in connection with the therapy delivery system of the present invention;

FIG. 13B is an illustration of a balloon fixation device usable in connection with the therapy delivery system of the present invention;

DETAILED DESCRIPTION OF THE PREFERRED EMBODIMENTS

The objects and advantages enumerated above, together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

An aspect of the present invention is the establishment of a tissue structure circulatory compartment that is at least partially isolated from the systemic circulation of the body. For the purposes of the present invention, the term "tissue structure" may mean a cell structure of a mammalian body, such as an organ or limb having blood circulation therethrough. The terms "organ" and "tissue structure" may therefore be used interchangeably herein to refer to a cell structure of or in a mammalian body through which sanguinous fluid is circulated. For the purposes of the present invention, the term "systemic" may mean the overall blood circulation of the mammalian body. An aspect of the present invention, therefore, is to at least partially separate blood circulation of a tissue structure from the remainder of the systemic circulation. By at least partially isolating the tissue structure circulation, localized tissue structure therapy and/or tissue structure protection may be realized.

The present invention may be directed to delivering therapy through the venous system of the target tissue structure to maximize the effects of localized treatment, and to at least partially isolate the tissue structure circulation from the systemic circulation to minimize or prevent therapy dilution and/or systemic side effects. The venous system provides a relatively safe and direct access to a tissue structure and its capillary bed, without the risks associated with access to the arterial system. The approach of the present invention may be used in various applications, including tissue structure-localized therapeutic hypothermia, drug delivery, chemotherapy, and cell-based therapy. Moreover, the present invention may be employed to protect vulnerable tissue structures from systemic treatments, such as renal failure from systemic chemotherapy. A still further application of the present invention is local organ plasma paresis or organ dialysis for large organs with severe injury that could cause secondary systemic injury.

In some embodiments, therapy deactivation may be beneficial in minimizing or eliminating systemic impact of the delivered therapy. Therapy deactivation may include, for example, warming cooled blood to physiologic temperature, metabolizing bioactive agents to minimize or eliminate toxins in the bioactive agents, and adding compensatory agents to neutralize systemic activity of bioactive agents employed in the therapy.

Figure 1:
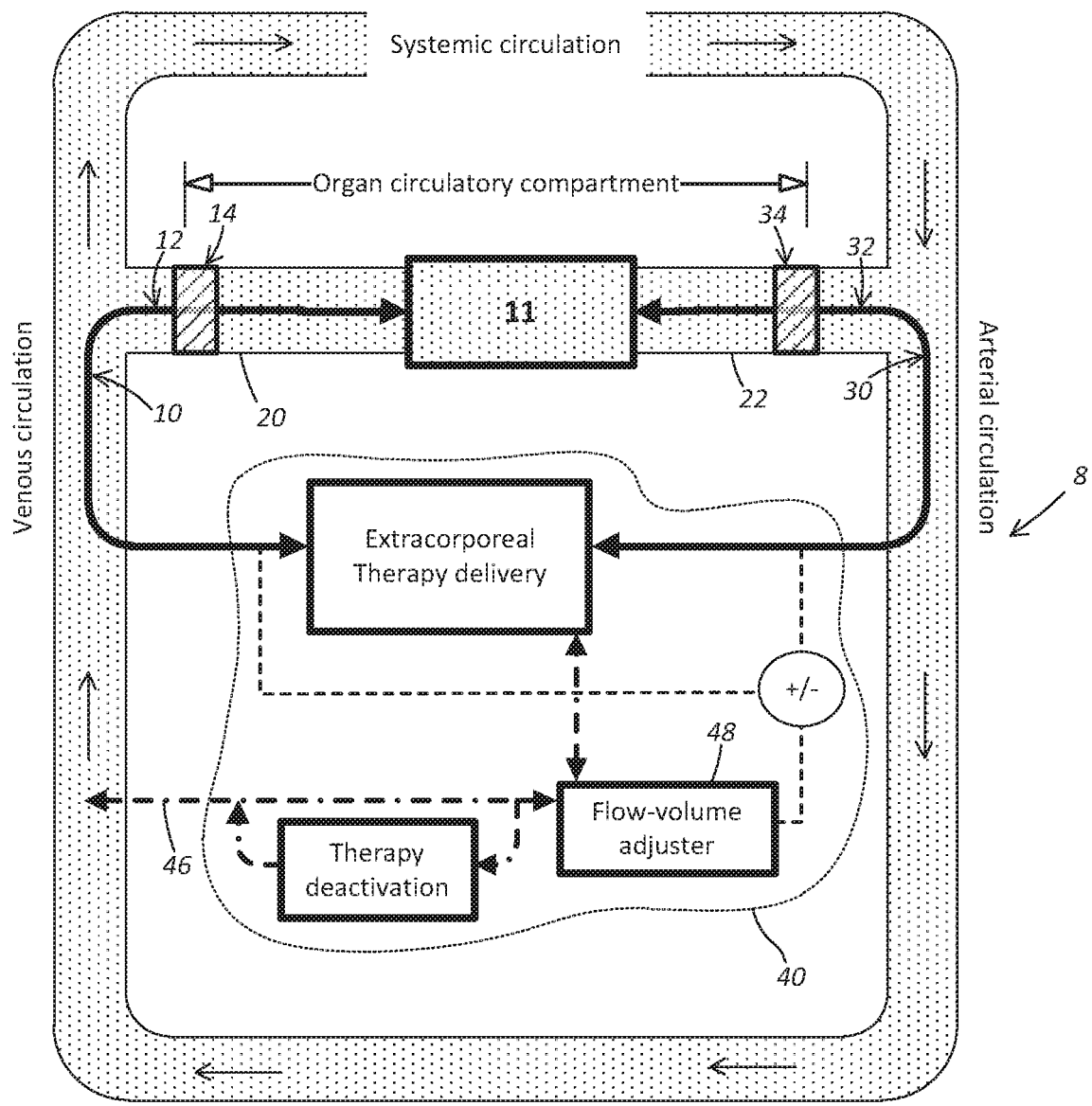
FIG. 1 is a schematic diagram of a therapy delivery system of the present invention.

In one aspect of the present invention, circulation of a tissue structure may be substantially completely isolated from the systemic circulation. A schematic diagram of a complete tissue structure isolation arrangement is shown in FIG. 1, in which catheters may be inserted into an arterial inflow structure and a venous drainage structure of a target tissue structure (organ). The catheters each include an occlusion device that is adapted to selectively substantially occlude the respective arterial inflow structure or venous drainage structure to thereby substantially occlude all arterial or venous flow therethrough. Once placement of the catheters and respective occlusion devices are deployed to complete the circulatory isolation of the target tissue structure, an extracorporeal blood conditioning apparatus is provided to provide local blood circulation to the target tissue structure.

The schematically illustrated complete isolation system 8 includes a venous catheter 10 having a distal portion 12 positionable at a venous drainage structure 20 of the target tissue structure 11. Distal portion 12 of venous catheter 10 includes a first occlusion device 14 that is adapted to selectively substantially occlude venous drainage structure 20, and to thereby substantially occlude all venous drainage of tissue structure 11.

As illustrated in FIG. 1, the flow direction of the circulation may be antegrade (artery to vein) or retrograde (vein to artery). In embodiments employing retrograde flow and complete tissue structure isolation, the arterial circulation may be used as the drainage of the organ (tissue structure) circulatory compartment. Retrograde flow through the organ circulatory compartment may be somewhat preferred over antegrade flow, in that venous systems typically have more collateral circulation than do arterial systems. As a result, retrograde flow may provide more access to the organ tissues and its capillary bed than antegrade flow. Moreover, retrograde perfusion may have better access to a post-occlusion ischemic area of the target organ (tissue structure). Retrograde flow may additionally minimize arterial damage and the potential for debris occlusion through arterial embolism, as compared to antegrade flow through the organ circulatory compartment. Because the organ circulation is controlled independently from the systemic circulation, flow rate and pressure of perfusion of the organ may be independently optimized to achieve maximum tissue perfusion or therapy exchange at the cellular level. Bi-directional flow through the organ circulatory compartment (alternating between antegrade and retrograde flow) may also be beneficial to minimize vessel occlusion for prolonged uses of the therapy delivery of the present invention.

A blood conditioning apparatus within an extracorporeal blood loop is provided in the system of the present invention to condition autologous blood for perfusion through the organ circulatory compartment. The blood conditioning apparatus for extracorporeal therapy delivery may include a flow-volume adjusting mechanism to regulate or equate input and output blood volumes to the organ circulatory compartment. The flow-volume adjusting mechanism monitors input/output balance, and is adapted to selectively add or remove blood to or from the organ circulation loop, with the balancing blood sourced from the systemic circulation. In this manner, the flow-volume adjusting mechanism is adapted to balance the input/output flow through the target organ.

In some embodiments, the blood conditioning apparatus is further adapted to condition blood exiting the organ circulatory compartment and entering the systemic circulation. Such conditioning is schematically illustrated in FIG. 1 as "therapy deactivation", wherein the blood conditioning apparatus deactivates therapy that has passed through the target organ in the organ circulation loop. Deactivation of the delivered therapy may be beneficial prior to returning blood flow to the systemic circulation to minimize or eliminate systemic impact of the therapy.

Figure 2:
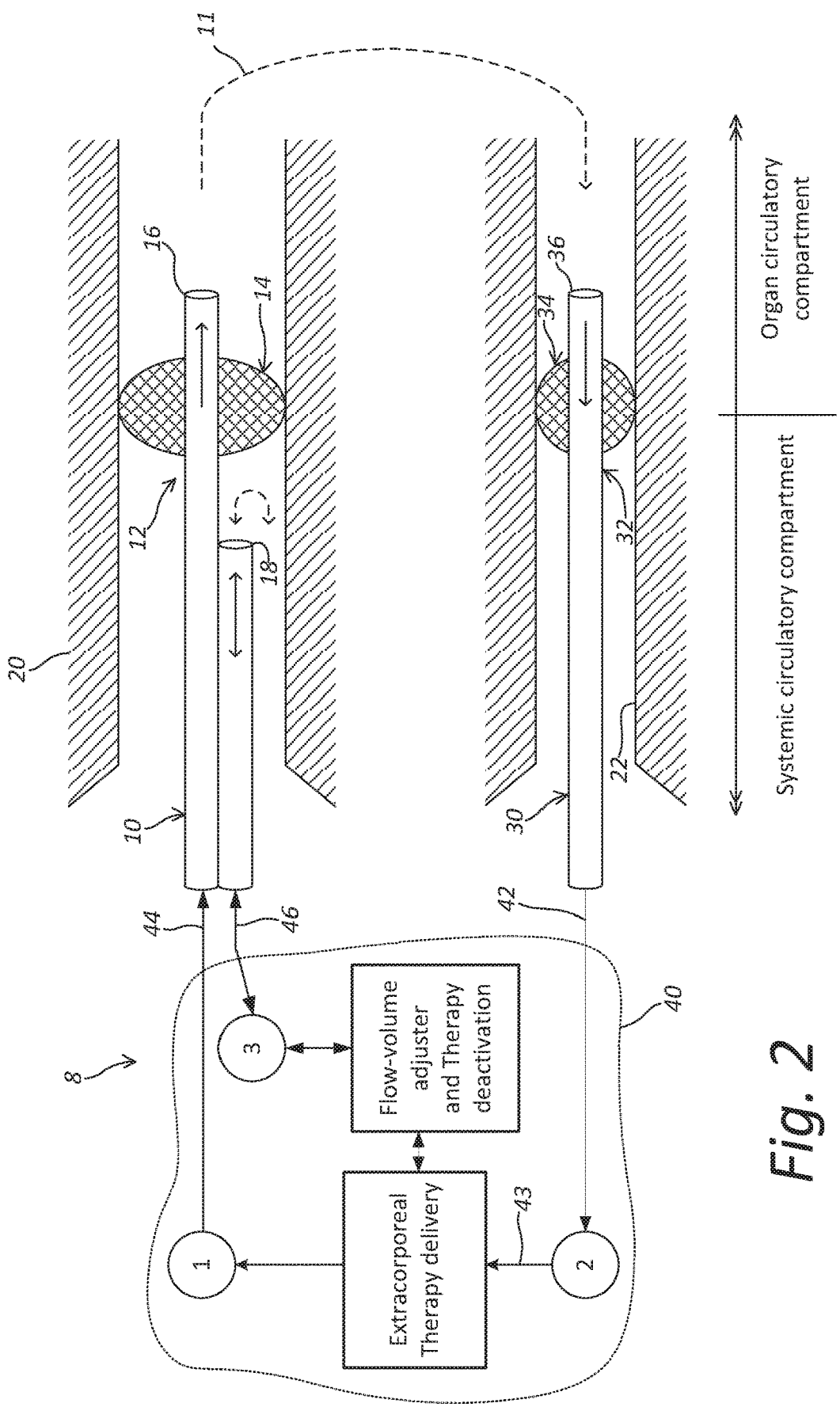
FIG. 2 is a schematic illustration of the system depicted in FIG. 1.

An implementation of the complete organ isolation arrangement schematically set forth in FIG. 1 is illustrated in FIG. 2, wherein system 8 includes a venous catheter 10 having a distal portion 12 that is positionable at a venous drainage structure 20 at a target tissue structure (organ) 11. Distal portion 12 of venous catheter 10 includes a first occlusion device 14 that is adapted to selectively substantially occlude venous drainage structure 20, and to thereby substantially occlude all venous drainage of tissue structure 11. Venous catheter 10 further includes a perfusion port 16 that is operably disposed upstream from first occlusion device 14, and a systemic port 18 operably disposed downstream from first occluder device 14.

For the purposes of the present invention, the terms "upstream" and "downstream" refer to the natural, unaltered blood flow direction, such as the natural, unaltered blood flow directions through arteries, organs, and veins. Therefore, the term "upstream" in a venous drainage structure means in a relative direction toward the respective tissue structure/organ from which venous blood flow is drained through such venous drainage structure. Therefore, even in the case of retrograde perfusion (such as that illustrated in FIG. 2), a perfusion port (16) disposed "upstream from" an occlusion device (14) is intended to mean that such perfusion port (16) is proximally located to the target tissue structure (11) with respect to the occlusion device (14).

System 8, as illustrated in FIG. 2, further includes an arterial catheter 30 having a distal portion 32 positionable at an arterial inflow structure 22 of tissue structure 11. Distal portion 32 of arterial catheter 30 includes a second occlusion device 34 that is adapted to selectively substantially occlude arterial inflow structure 22, and to thereby substantially occlude all arterial inflow of tissue structure 11. Arterial catheter 30 further includes a drainage port 36 that is operably disposed downstream from the second occlusion device 34.

In some embodiments, second occlusion device 34 substantially occludes all arterial inflow to tissue structure 11, and first occlusion device 14 substantially occludes all venous drainage from tissue structure 11. However, it is contemplated that system 8 may be employed for tissue structures 11 having collateral circulation on one or both of the arterial and venous systems. Accordingly, the first and second occlusion devices 14, 34 of system 8 may be employed to occlude only targeted venous drainage structures and arterial inflow structures of tissue structure 11. Moreover, while systemic port 18 is illustrated in FIG. 2 as being associated with venous catheter 10, it is contemplated that systemic port 18 may be associated with either or both of venous catheter 10 and arterial catheter 30.

System 8 further includes a blood conditioning apparatus 40 which fluidly couples together perfusion port 16, drainage port 36, and systemic port 18. Blood conditioning apparatus 40 is capable of conditioning blood supply thereto as drainage flow 42 through drainage port 36 and drainage line 2, reperfusing at least a portion of drainage flow 42 through perfusion line 1 and perfusion port 16 as conditioned retrograde perfusion flow 44, and dispensing at least a portion of drainage flow 42 through systemic line 3 and systemic port 18 as systemic flow 46. As indicated above, a flow-volume adjusting mechanism 48 may be employed to increase/decrease blood flow in the organ circulatory compartment to maintain desired blood flow and fluid pressures within the organ circulatory compartment. Consequently, flow-volume adjusting mechanism 48 is capable of permitting and/or motivating blood flow either to the systemic circulatory compartment out through systemic port 18, or in from the systemic circulatory compartment through systemic port 18 along systemic line 46. Consequently, blood flow may be bi-directionally processed through systemic line 46 to accommodate the adjustment controlled by flow-volume adjusting mechanism 48 of blood conditioning apparatus 40. Such bi-directionality is schematically depicted in FIG. 1. Typically, flow-volume adjusting mechanism 48 is required only in complete tissue structure isolation embodiments of the present invention, such as that illustrated in FIGS. 1 and 2, in which arterial inflow and venous outflow from tissue structure 11 is substantially completely controlled by at least venous catheter 10 and arterial catheter 30 of system 8. It is also to be understood that flow-volume adjusting mechanism 48 is not a required component of system 8, but rather an optional mechanism for control of blood flow to and from the organ circulatory compartment. It is also to be understood from the schematic depiction of FIG. 1 that blood flow through the target organ, as driven by system 8, may be retrograde, antegrade, or alternating between retrograde and antegrade. For antegrade flow through the target organ 11, perfusion of conditioned blood may be dispensed by blood conditioning apparatus 40 through line 2, and drained from organ 11 through line 1. It should therefore be understood that the roles of at least the perfusion and drainage lines of system 8 may be reversed for antegrade and/or bi-directional flow through target organ 11.

As depicted in FIG. 2, system 8 employs two separate catheters, 10, 30, and two vascular access points. In the illustrated embodiment, arterial catheter 30 is a dual lumen balloon catheter, with second occlusion device 34 being an inflatable occlusion balloon as commonly utilized in the art. A first lumen of arterial catheter 30 is drainage line 2, while a second lumen may be utilized for balloon inflation and deflation. The first and second occlusion devices 14, 34 may each be inflatable balloons to separate the organ circulation from the systemic circulation, resulting in separated organ and systemic circulatory compartments. Perfusion port 16 and drainage port 36 are open in the organ circulatory compartment, while the systemic port 18 is open to the systemic circulatory compartment. Venous catheter 10 may be a triple lumen balloon catheter, with a first lumen dedicated for perfusion line 1, a second lumen dedicated for systemic line 3, and a third lumen for balloon inflation and deflation. In one embodiment, systemic line 3 may be incorporated with venous catheter 10 in order to minimize the possibility of arterial embolism.

Catheters 10, 30 may be inserted through any common venous or arterial accesses, respectively, such as the femoral, internal jugular, or subclavian vein, or the femoral or carotid artery. In a particular embodiment, arterial catheter 30 may be a stent delivery catheter or a thrombectomy catheter having arterial access. To connect drainage port 36 and drainage flow 42 to blood conditioning apparatus 8, a shunt 43 may be employed.

For certain implementations, the arterial catheterization required for the complete organ circulatory isolation system described in FIGS. 1 and 2 may be undesirable for its potential complications of arterial embolism to the target organ itself or to other vital organs, and/or may not be feasible in certain clinical situations, such as in an emergency. The present invention, therefore, also contemplates a partial organ circulatory compartment isolation using only venous access to perform the therapy delivery. Venous access may be achieved through minimally invasive techniques, and is relatively rapidly achievable, even in an emergency setting.

Partial organ circulatory isolation, unlike complete isolation techniques described above, do not require arterial access. Perfusate for therapy delivery may be applied retrogradedly through the venous drainage structure of the target tissue structure (organ). In this approach, the organ experiences somewhat increased blood flow and fluid pressure. Veins typically exhibit relatively high elastic compliance, and are therefore well suited to accommodate the increased blood flow and pressure of the retrograde perfusion techniques of the present invention. Increased organ venous pressure may actually be advantageous in increasing hydrostatic pressure and tissue perfusion, thereby minimizing no-flow phenomena caused by an ischemic event, and increasing oxygenated blood flow to the post-arterial occlusive area. Partial circulatory isolation may be performed by diverting normal venous flow through a venous drainage line to an extracorporeal blood conditioning apparatus to condition the blood (oxygenating, cooling, bioactive agent addition, etc.) and perfusing the conditioned sanguineous material through a perfusion line to the venous drainage structure of the target tissue structure. In this manner, the accessed vein is "arterialized" to supply the target organ with additional oxygenated blood flow. Since the arterial flow to the target tissue structure contributes to the flow volume of the venous drainage where the arterial inflow is not occluded, only a certain fraction of the venous drainage flow volume is returned to the extracorporeal therapy delivery and reperfused to the target organ through the venous perfusion line. Excess venous blood volume captured by the venous drainage line of the present system may be directed to the systemic circulation, and optionally through a therapy deactivation system prior to return to the systemic circulation. A schematic representation of an embodiment of the present invention for partial tissue structure circulatory isolation is provided in FIG. 3. System 60 includes a first venous access line 64 positionable at a first venous drainage structure 72 of a target tissue structure 61, and a second venous access line 66 positionable at a second venous drainage structure 74 of tissue structure 61. In one embodiment, first venous access line 64 is a first venous catheter having a distal portion 65 that is positionable at first venous drainage structure 72 of tissue structure 61. Distal portion 65 of first venous catheter 64 may include a first occlusion device 68 that is adapted to selectively substantially occlude first venous drainage structure 72. FIG. 4 provides a more detailed illustration of the system 60 schematically depicted in FIG. 3.

Second venous access line 66 may be a second venous catheter having a distal portion 67 that is positionable at second venous drainage structure 74. Distal portion 67 of second venous catheter 66 may include a second occlusion device 78 that is adapted to selectively substantially occlude second venous structure 74 so as to, in combination with first occlusion device 68, establish an organ circulatory compartment of tissue structure 71 that is separate from the systemic circulatory compartment. In some embodiments, however, first and second catheters 64, 66 only partially occlude venous drainage of tissue structure 61, and are therefore useful in isolating at least portions of tissue structure 61 for preferred conditioned blood perfusion thereof.

Figure 3:
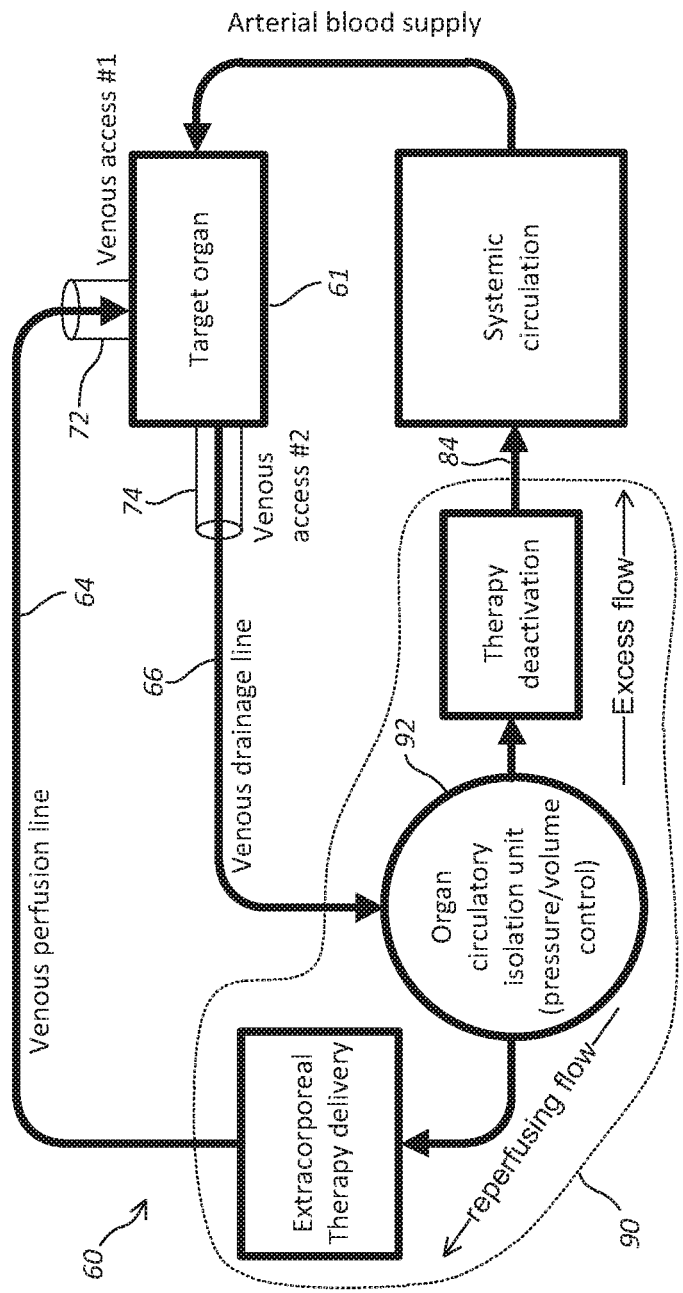
FIG. 3 is a schematic diagram of a therapy delivery system of the present invention.
Figure 4:
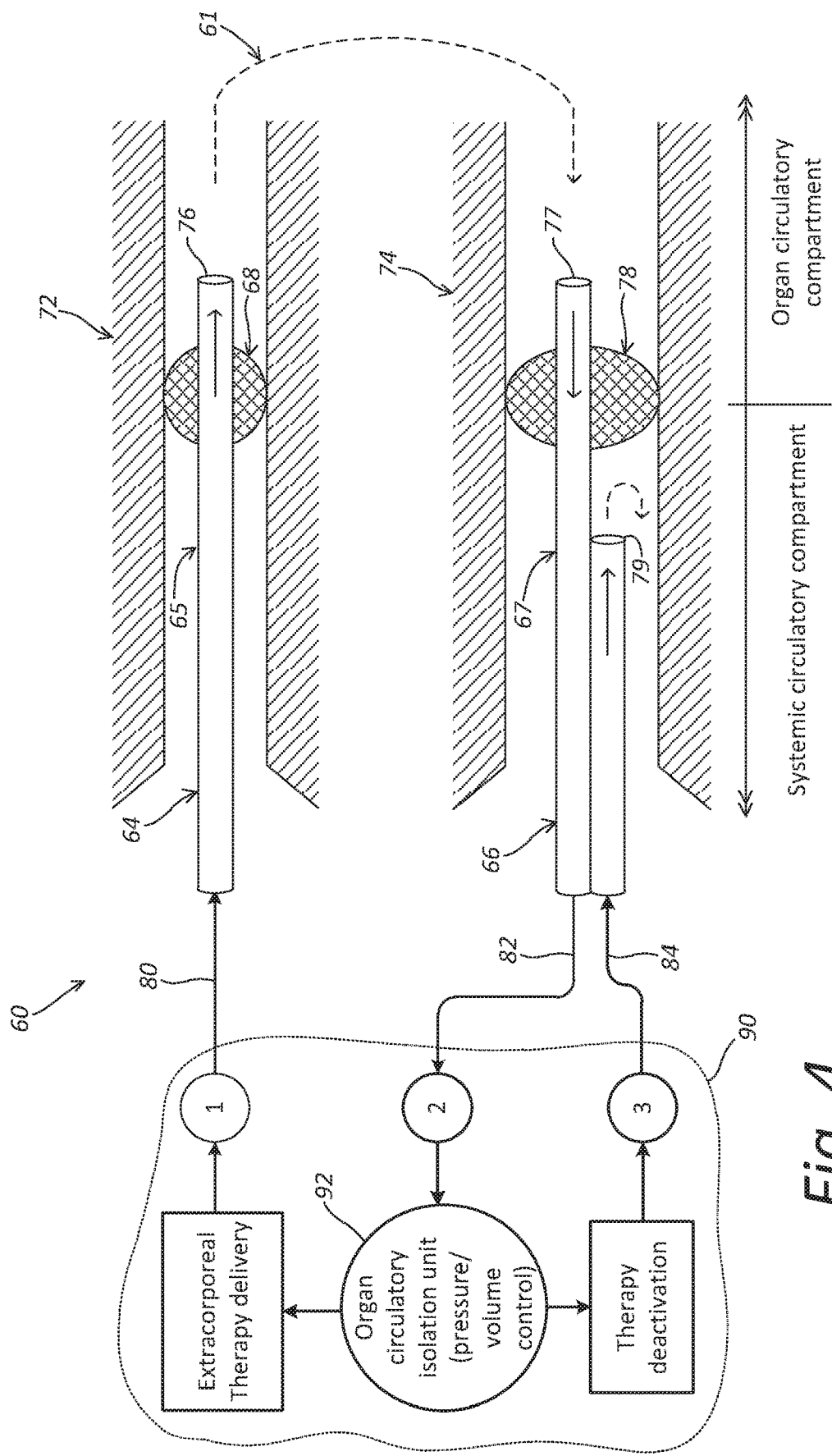
FIG. 4 is a schematic illustration of the system depicted in FIG. 3.

In the schematic diagram of FIG. 3, first venous access line 64 may accommodate a venous perfusion line 1 for perfusion flow 80, while second venous access line 66 may accommodate a drainage line 2 for venous drainage flow 82. First and second catheters 64, 66 may include a perfusion port 76 operably disposed upstream from a respective one of first and second occlusion devices 68, 78. First and second catheters 64, 66 may further include a drainage port 77, and a systemic port 79 that is operably disposed downstream from a respective one of first and second occlusion devices 68, 78.

System 60 further includes a blood conditioning apparatus 90 which fluidly couples perfusion port 76, drainage port 77, and systemic port 79 to one another at an organ circulatory isolation unit 92 of blood conditioning apparatus 90. In this embodiment, blood conditioning apparatus 90 is capable of conditioning blood supplied thereto as drainage flow 82 through drainage port 77 and drainage line 2 and reperfusing at least a portion of drainage flow 82 through perfusion line 1 and perfusion port 76 as conditioned retrograde perfusion flow 80. Conditioning apparatus 90 is further configured to dispense at least a portion of drainage flow 82 through systemic line 3 and systemic port 79 as systemic flow 84. As with other embodiments of the present invention, it is to be understood that systemic line 3 terminating in systemic port 79 may be incorporated with either or both of first and second catheters 64, 66. Moreover, it is to be understood that either or both of first and second catheters 64, 66 may include one or both of perfusion line 1 terminating in perfusion port 76 and drainage line 2 originating from drainage port 77.

In the illustrated embodiment, perfusate is directed to tissue structure 61 and its capillary bed through perfusion line 1, and returns from tissue structure 61 through venous drainage line 2 via venous collateral circulation between first and second venous drainage structures 72, 74 of tissue structure 61. In this manner, the two veins 72, 74 operate as a perfusion vein and a drainage vein, respectively. In some embodiments, a small negative pressure on drainage line 2 may be provided to draw most of the venous blood flow of tissue structure 61 to drainage port 77.

As described above with respect to the complete isolation embodiment, system 60, employing at least two venous access locations, may be employed for either of complete or partial tissue structure circulation isolation. First and second catheters 64, 66 may be multiple lumen balloon catheters, wherein first and second occlusion devices 68, 78 may be inflatable balloons, as is well known in the art. For the illustrated example, first catheter 64 may be a dual-lumen catheter, with a first lumen for profusion line 1, and a second lumen for transporting fluid for inflation/deflation of balloon 68. In similar manner, second catheter 66 may be a triple-lumen catheter, with a first lumen for drainage line 2, a second lumen for systemic line 3, and a third lumen for transporting inflation fluid to inflatable balloon 78. With occlusion devices 68, 78 deployed in an occluding condition, perfusion and drainage lines 1, 2 are open in the organ circulatory compartment, while the systemic line 3 is open to the systemic circulatory compartment.

In the illustrated embodiment, drainage port 77 is disposed upstream from a respective one of first and second occlusion devices 68, 78. However, it is contemplated that drainage port 77 may be disposed downstream from first and second occlusion devices (in the systemic circulatory compartment), particularly in applications where tissue structure 61 possesses collateral venous drainage in addition to first and second venous drainage structures 72, 74.

The multiple access catheter configuration of system 60 permits simultaneous perfusion and drainage for continuous therapy delivery. Though continuous, the venous retroperfusion and drainage flows, separately, may be constant or cyclical, and may be regulated by systemic or local hemodynamic or safety pressure set points monitored by blood conditioning apparatus 90 in a manner described in more detail hereinbelow.

Ideal tissue structure candidates for system 60 may include at least two major venous drainage lines. A particular example is the brain which has venous drainage to the left and right internal jugular veins, which are well connected through intracranial venous sinuses. As a result, perfusion through one internal jugular vein may effectively perfuse both sides of the brain, and venous return flow from both sides of the brain can be drained to another internal jugular vein, without significant increase of intracranial or intracerebral pressure. Internal jugular vein catheterization is also a common intervention, such that system 60 of the present invention may be readily accepted by practicing physicians.

One example application of system 60 may be in providing therapeutic hypothermia to global brain tissue. Full-time balloon inflation for first and second balloon catheters 64, 66 establishes an environment conducive to localized brain cooling, and minimizes systemic cooling. One or more of catheters 64, 66 may be provided with a pressure sensor, such that the respective occlusion devices 68, 78 may be intermittently deflated to release potential backflow to the cerebral circulation. In this embodiment, conditioning by blood conditioning apparatus includes cooling perfusion flow 80 to less than about 35° C. Moreover, blood conditioning apparatus 90 may incorporate therapy deactivation, such that conditioning further includes warming systemic flow 84 to physiologic temperature to avoid undesirable systemic cooling.

Figure 5:
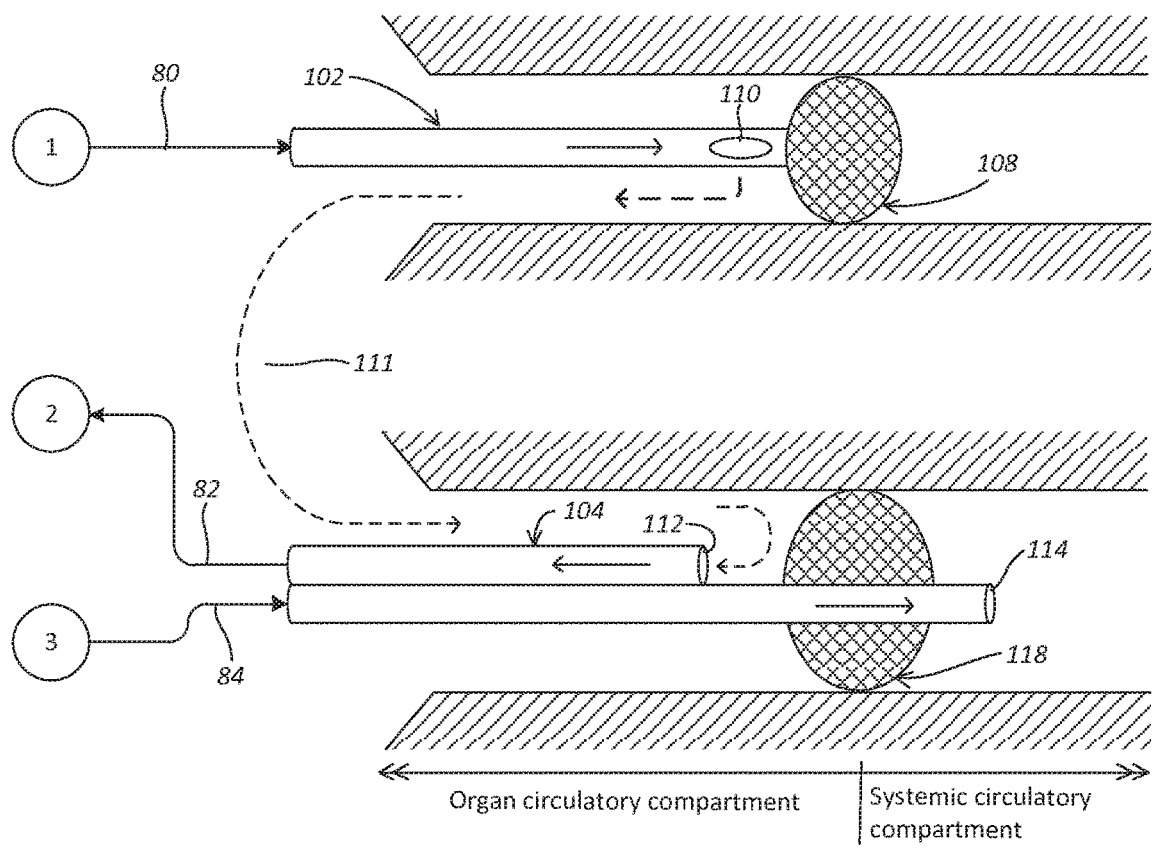
FIG. 5 is a schematic illustration of the system depicted in FIG. 3.

Another embodiment of the present invention is illustrated in FIG. 5, wherein first and second catheters 102, 104 are configured for venous access from an opposite direction as that described with respect to first and second catheters 64, 66. In particular, first catheter 102 may be arranged such that first occlusion device 108 is distally disposed with respect to perfusion port 110, with perfusion port 110 operable disposed upstream from first occlusion device 108 (in the organ circulatory compartment). Perfusion flow 80 therefore is dispensed out from perfusion port 110 to perfuse tissue structure 111 in a retrograde direction. In the embodiment illustrated in FIG. 5, second catheter 104 includes a drainage port 112 disposed upstream from second occlusion device 118 (in the organ circulatory compartment), such that perfusion port 110 and drainage port 112 are open to the organ circulatory compartment, while systemic port 114 is open to the systemic circulatory compartment.

Figure 6:
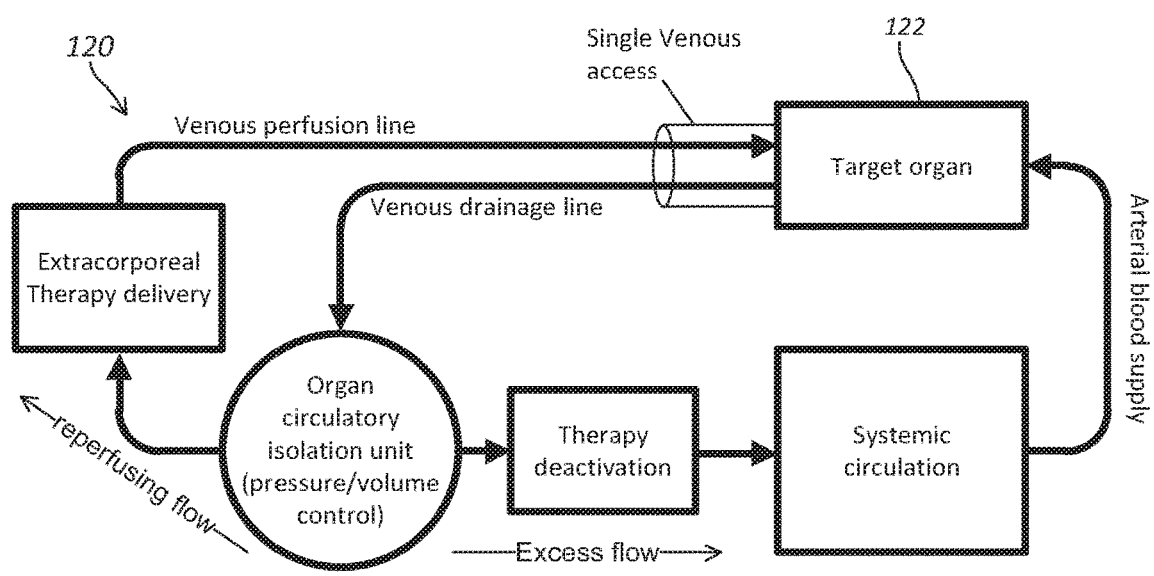
FIG. 6 is a schematic diagram of a therapy delivery system of the present invention.

A further embodiment of the present invention is schematically depicted in FIG. 6, wherein system 120 includes a single venous access line that is adapted to deliver localized therapy to an at least partially isolated target tissue structure 122. A more detailed depiction of system 120 is illustrated in FIG. 7. The single venous access line may be embodied in a venous catheter 124 having a distal portion 126 that is positionable at a venous drainage structure 140 of tissue structure 122. Distal portion 126 of catheter 124 may include an occlusion device 128 that is adapted to selectively substantially occlude venous drainage structure 140. In one embodiment, occlusion device 128 may be deployed to substantially isolate venous circulation of tissue structure 122 from the systemic body circulation, so as to separate an organ circulatory compartment from the systemic circulatory compartment (as illustrated in FIG. 7). In some embodiments, catheter 124 includes a perfusion port 132 operably disposed upstream from occlusion device 128 for dispensing perfusate to the localized organ circulatory compartment. Catheter 124 preferably further includes a drainage port 134 for capturing venous drainage flow 144 to supply system 120 with blood flow for generating a conditioned perfusate. Drainage port 134 may be disposed upstream or downstream from occlusion device 126, as desired per application. Embodiments utilizing drainage port 134 downstream from occlusion device 128 may involve tissue structures 122 with collateral venous discharge and/or intermittent deployment of occlusion device 128. In this manner, venous drainage from tissue structure 122 may be mediated to maintain fluid pressures at tissue structure 122 within acceptable limits.

The arrangement illustrated in FIG. 7 is an example organ circulatory isolation configuration, wherein at least a venous drainage structure 140 of tissue structure 122 may be continuously occluded by occlusion device 128, and wherein therapy delivered through perfusion line 1 and through perfusion port 132 may be substantially completely captured at drainage port 134 upstream from occlusion device 128. As a consequence, perfused therapy is substantially maintained within the organ circulatory compartment, and does not contaminate the systemic circulatory compartment.

System 120 further includes a blood conditioning apparatus 150 which fluidly couples perfusion port 132 and drainage port 134 to one another. Blood conditioning apparatus 150 may be capable of receiving blood supply thereto as drainage flow 144 through drainage port 134, and reperfusing at least a portion of drainage flow 144 through perfusion port 132 as conditioned retrograde perfusion flow 132. The conditioning of conditioning apparatus 150 may include providing cooling to generate perfusion flow 142 at less than about 35° C.

In some embodiments, catheter 124 includes a systemic port 136 operably disposed in the systemic circulatory compartment, and fluidly connected to perfusion port 132 and drainage port 134 through blood conditioning apparatus 150. Blood conditioning apparatus 150 may be capable of dispensing at least a portion of drainage flow 144 through systemic port 136 as systemic flow 146. Systemic port 136 is preferably arranged to dispense systemic flow 146 into the systemic circulatory compartment. Prior to dispensing systemic flow 146 into the systemic circulatory compartment, blood conditioning apparatus 150 may condition systemic flow 146 by deactivating systemic flow 146. In some embodiments, deactivation by blood conditioning apparatus 150 includes warming systemic flow 146 to physiologic temperature. In this manner, hypothermic therapy delivered to the targeted tissue structure 122 within the organ circulatory compartment may be "deactivated", or warmed, prior to release to the systemic circulatory compartment, such that the therapeutic hypothermia is localized to the target tissue structure 122, and does not contaminate the systemic circulatory compartment.

System 120 illustrated in FIG. 7 provides retrograde therapy delivery to the targeted tissue structure 122, and controls venous drainage through drainage port 134 to direct venous drainage flow 134 to blood conditioning apparatus 150. In some embodiments, single catheter 124 may be positioned within a venous drainage structure of tissue structure 122 that accounts for substantially all venous drainage from tissue structure 122. An example embodiment is in therapy delivery to the myocardium by placement of catheter 124 at the coronary sinus, such that occlusion device 128 occludes substantially all venous drainage from the myocardium. Such an arrangement prevents or minimizes contamination of the therapy between the coronary and systemic circulations. Occlusion device 128, which may be an inflatable balloon of a balloon catheter, may be continuously deployed in contact with the coronary sinus wall to establish true compartmentalization of the coronary circulatory system, as separate from the systemic circulatory compartment.

The embodiment illustrated in FIG. 8 exhibits similar functionality to the embodiment illustrated in FIG. 7, but with a somewhat modified configuration. In particular, single catheter 160 may be arranged with systemic port 168 operably disposed distally of occlusion device 170, such that systemic flow 146 is dispensed through systemic line 3 and out from systemic port 168 into the systemic circulation. In this embodiment, occlusion device 170 substantially completely isolates venous drainage of the target organ from systemic circulation, wherein occlusion device 170 substantially occludes a main, or only, venous drainage structure 140 of the target tissue structure 122. Perfusion flow 142 is dispensed at perfusion port 162 proximally of occlusion device 170, but nevertheless within the venously isolated organ circulatory compartment. Likewise, venous drainage from tissue structure 122 through drainage port 164 for drainage line 144.

In either of the embodiments illustrated in FIGS. 7 and 8, the venous drainage of the organ circulatory compartment may be substantially isolated from the systemic circulatory compartment. Consequently, therapy may be delivered through perfusion line 1 to the organ circulatory compartment for localized therapy of the targeted tissue structure 122. Due to the substantial isolation of venous drainage from tissue structure 122, the delivered therapy may be kept separated from the systemic circulatory compartment, and processed through the blood conditioning apparatus prior to return to the systemic circulatory compartment. Targeted therapy may therefore be accomplished in a localized manner to the target organ/issue structure, without incurring undesired side effects through contamination of the therapy to systemic circulation.

In addition to providing localized therapy to a target tissue structure, the configurations described above provide a simple, single-catheter device for accomplishing the localized therapy. The single catheter arrangement requires only a single venous access, which may be rapidly performed, even under emergent situations. Distal placement of the single catheter is also facilitated through the requirement of only a single occlusion device strategically positioned to selectively substantially occlude venous drainage from the targeted tissue structure.

Figure 9:
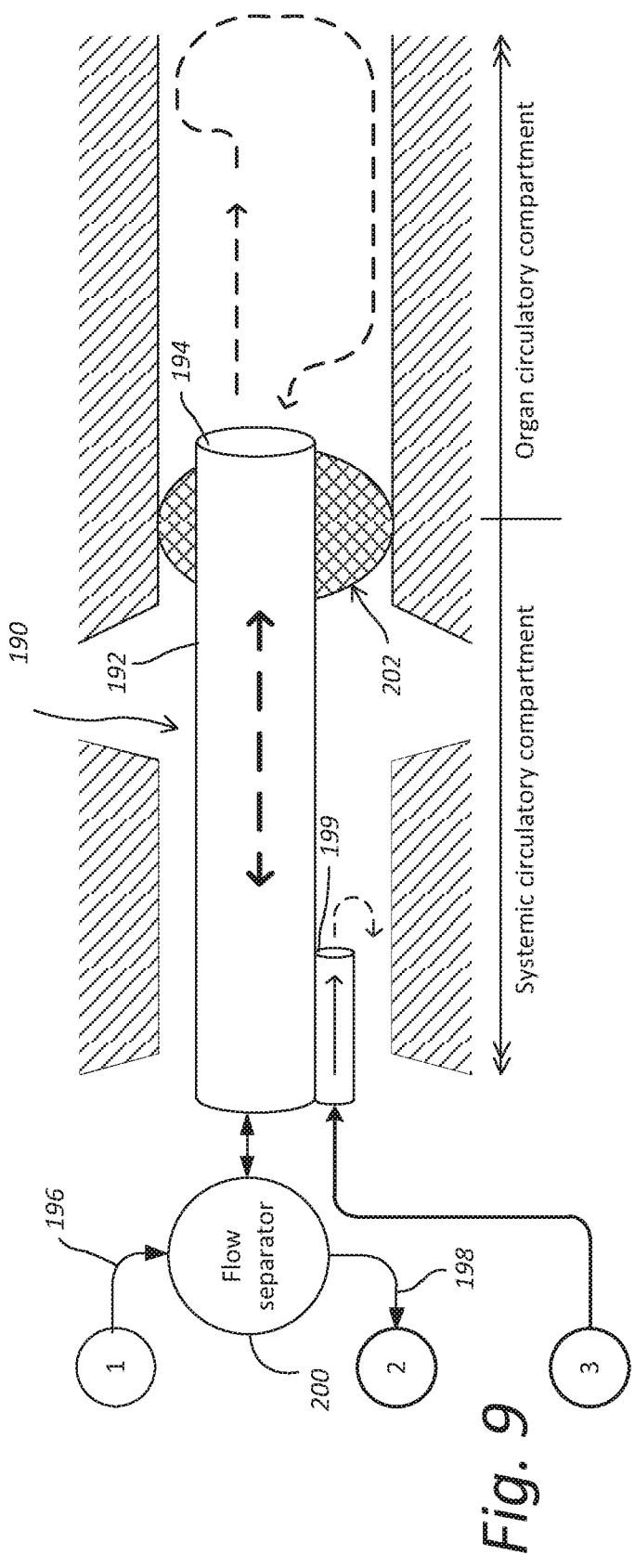
FIG. 9 is a schematic illustration of the system depicted in FIG. 6.
Figure 10:
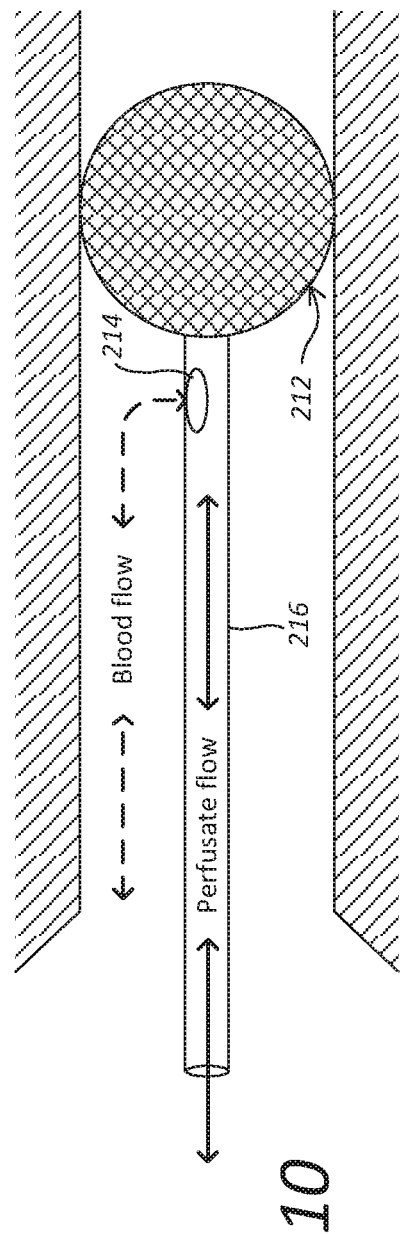
FIG. 10 is a schematic illustration of the system depicted in FIG. 6.

It is also contemplated by the present invention that the perfusion and drainage lines 1, 2 may be combined into a single lumen for communication with a combined perfusate/drainage port operably disposed in the selectively substantially isolated organ circulatory compartment. A first example of such an embodiment is illustrated in FIG. 9, in which catheter 190 includes a combined perfusion/drainage lumen 192 communicating with a combined perfusion/drainage port 194 disposed in the organ circulatory compartment, and selectively substantially isolated from the systemic circulatory compartment by occlusion device 202. In the embodiment illustrated in FIG. 9, combined perfusion/drainage port 194 is operably disposed distal to occlusion device 202. The embodiment of FIG. 10 provides for a distally located occlusion device 212 with respect to combined perfusion/drainage port 214 of combined perfusion/drainage lumen 216. Combined perfusion/drainage port 214 of FIG. 10 is also disposed upstream from occlusion device 212, so as to communicate with the selectively substantially isolated organ circulatory compartment.

In either of the embodiments illustrated in FIGS. 9 and 10, the perfusion and drainage flows 196, 198 are separated in a flow separator device 200 within the blood conditioning apparatus. Flow through lumens 192, 216, therefore, is bi-directional, in perfusing in a retrograde direction, and permitting antegrade drainage of venous flow to the blood conditioning apparatus. Typically, a combined perfusion/drainage lumen 192, 216 may be employed for relatively larger-volume tissue structures/organs, particularly where the tissue structure volume is larger than the volume of the combination perfusion/drainage lumen 192, 216. A benefit of combining the perfusion and drainage lines 196, 198 into a single lumen 192, 216 is the reduction of flow resistance as a result of an increased luminal diameter. Such reduced flow resistance may facilitate increased perfusion and drainage flow. By contrast, the separated perfusion and drainage lumens of FIGS. 7 and 8 may be advantageously employed in certain applications to prevent a dead space for therapy exchange, particularly in small-volume target organs. Moreover, separating the perfusion line 1 from the drainage line 2 allows for the respective perfusion and drainage flows to have some overlap, and could therefore theoretically optimize or maximize therapy delivery. It is contemplated, therefore, that the present invention encompasses at least the illustrated configurations.

The systemic line 3, which communicates systemic port 199 to the systemic circulatory compartment may be variously arranged. For example, the systemic port location may vary from immediately proximal to the catheter insertion site, to a location adjacent to the operable location of the occlusion device, such as within the venous drainage structure of the organ downstream from the deployed occlusion device.

Each of the example embodiments of FIGS. 7-10 conceptually follow the schematic depiction of a single-vein access system illustrated in FIG. 6. Such a system may employ partial or complete isolation of the target tissue structure/organ 122, wherein arterial occlusion may or may not be employed in combination with the single venous access approach. The arrangement of the schematic diagram of FIG. 6, however, utilizes both venous perfusion and drainage in a single vein/venous drainage structure. In some embodiments, perfusion and drainage do not occur simultaneously, and are instead cyclically controlled for bi-directional flow, alternating between perfusion to the organ circulatory compartment, and drainage from the organ circulatory compartment. The venous retroperfusion line perfuses a therapy through the venous structure to reach the target tissue structure capillary bed and tissue. Such venous retroperfusion may result in elevated intramural and intravenous pressure of the target organ/tissue structure. The venous drainage line is, therefore, responsible for maintaining the intramural and intravenous pressure within a designated safety range, and also for insuring adequate tissue circulation. The venous perfusion/drainage cycle may correspond to the localized organ circulatory cycle, such as the cardiac cycle for the myocardium, or a wave form cycle for other organs, such as the liver. That is, the drainage cycle may be activated by, for example, physiological signals such as an electrocardiogram signal (with appropriate time offset from R wave or both or either of surface or intracardiac electrocardiogram), local hemodynamic information (local flow or pressure waveforms), or a pressure set point, or the combination of different signals. The balance between the perfusion and drainage phases may be governed or driven by the blood conditioning apparatus, as described in greater detail hereinbelow.

The single-vein access isolation technique may be used with a variety of organs or other tissue structures that have major venous portal drainage. Example tissue structures include the coronary sinus, the internal jugular veins of the brain, the hepatic veins, and the renal vein. In the case of therapy delivered to the liver, for example, a localized therapy for each lobe may be possible, as the hepatic venous system is divided into right, middle, and left hepatic veins, which are all accessible from the inferior vena cava. A primary benefit of the single-vein access technique is the simplicity of intervention, in requiring only one catheter accessed through a commonly utilized venous access point. In embodiments utilizing intermittent perfusion, the therapy delivery may require relatively larger perfusion flow volume compared to the organ volume, possibly resulting in elevated intravenous and intramural pressures. It is therefore desired that pressure monitoring be incorporated with such systems to maintain pressures within a safety range.

The embodiments of FIGS. 7-10 may operate with full-time occlusion of a venous drainage structure of the target tissue structure. Such full-time occlusion may be accomplished by inflation of an inflatable balloon against the venous walls of the venous drainage structure. The full-time occlusion is facilitated by positioning the drainage port upstream from the occlusion device, such that venous drainage from the at least partially isolated tissue structure may be drained to the blood conditioning apparatus for reperfusion of conditioned blood flow to the organ circulation compartment and deactivation and dispensation to the systemic circulation.

In another embodiment of the present invention illustrated in FIGS. 11A and 11B, a single access venous catheter 220 includes a perfusion line 1 terminating in a perfusion port 222 that is operably disposed upstream from occlusion device 230. Catheter 220 further includes a drainage line 2 receiving venous drainage flow through drainage port 224. Excess drainage flow may be returned to the systemic circulation at systemic line 3 through systemic port 221. Drainage port 224 and systemic port 221 are operably disposed in the systemic circulation, which is selectively and at least partially isolated from the organ circulatory compartment upstream from occlusion device 230. Such an arrangement may provide a "pseudo-isolated" therapy delivery, in which therapy delivered through perfusion port 222 at the organ circulatory compartment may be venously drained to the systemic circulation without first being routed through blood conditioning apparatus for deactivation. Drainage port 224 and/or systemic port 221 may be operably positioned in the systemic circulatory compartment proximally to the site of catheter insertion, or may be more distally disposed, such as more proximal to occlusion device 230. There is no requirement that drainage port 224 and systemic port 221 be operably positioned in proximity to one another. The sequence of drainage port 224 and systemic port 221 typically depends on the local distribution of venous braches. In some embodiments, drainage port 224 may be upstream from systemic port 221.

Occlusion device 230, which may be an inflatable balloon, may be selectively inflated and deflated in concert with a venous drainage cycle of the target organ. In such a manner, occlusion device 230 may be selectively deflated during the natural venous drainage cycle to permit venous drainage out from the organ circulatory compartment, and subsequently re-inflated to occlude the venous drainage structure to facilitate retrograde perfusion between drainage cycles. In the example of the target organ being the myocardium, occlusion device 230 may be an inflatable balloon operably positioned at the coronary sinus. Balloon 230 may be operated to deflate during the coronary venous drainage (systole). Re-inflation of balloon 230 may occur during diastole to facilitate retroperfusion into the myocardium from perfusion port 222 at that time. Because balloon 230 is deflated during systole, therapy delivered through perfusion port 222 may be allowed to contaminate the systemic circulation to some extent. However, drainage port 224 may be arranged to continuously or cyclically collect contaminated systemic venous blood flow, and deactivate the delivered therapy at the blood conditioning apparatus for reentry to the systemic circulation at systemic port 221. In the case of therapeutic hypothermia of the myocardium, the deactivation performed by the blood conditioning apparatus may be to warm contaminated systemic blood flow and return systemic flow 3 at or above physiologic temperature. This method compensates for the therapy contamination permitted through the cyclic deflation of balloon 230.

Figure 12:
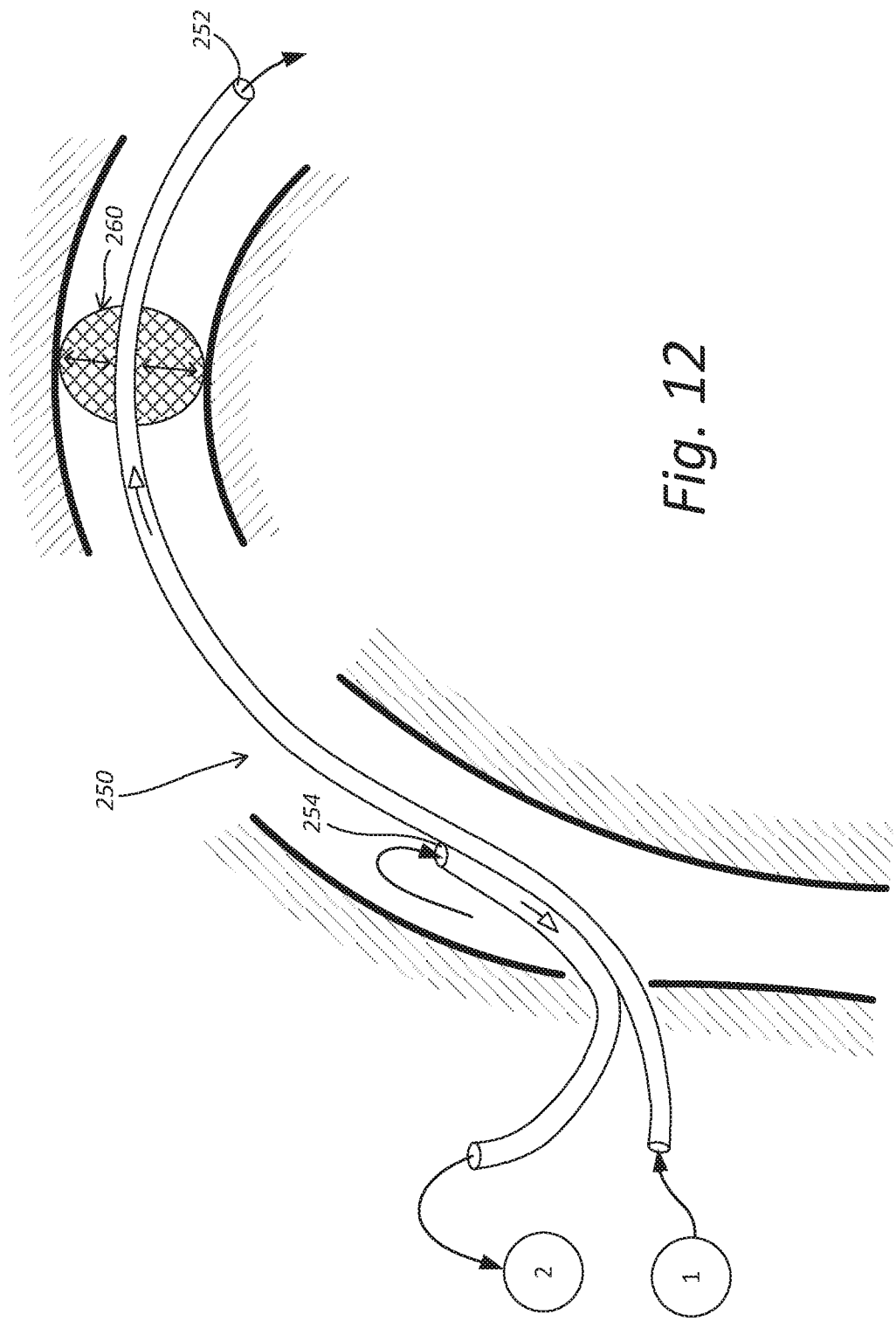
FIG. 12 is a schematic illustration of a therapy delivery system of the present invention.

Another embodiment of the present invention is illustrated in FIG. 12, wherein single access venous catheter 250 includes a perfusion line 1 terminating in a perfusion port 252 that is operably disposed upstream from occlusion device 260 in a venous drainage structure of a target organ/tissue structure. As such, perfusion port 252 may be operably disposed in an organ circulation compartment that is at least partially separated from the systemic circulation by occlusion device 260. Catheter 250 further includes a drainage line 2 collecting venous drainage flow through drainage port 254. Drainage line 2 may comprise a lumen having drainage port 254 disposed at any desired location, but may be preferably disposed along a venous pathway defined by catheter 250 at a location between the site of catheter insertion and the operating position of occlusion device 260. Drainage port 254 may be disposed in the systemic circulation at least partially separated from the organ circulation compartment in which perfusion port 252 is operably disposed.

Occlusion device 260 may be operated in a similar fashion as that described with respect to occlusion device 230 of catheter 220, wherein occlusion device 260 may be deployed in an occluding condition intermittently to permit cyclic venous drainage flow out from the organ circulatory compartment. The arrangement of FIG. 12 facilitates direct therapy delivery to the target tissue structure/organ. As with the embodiment of FIG. 11, perfusion through perfusion port 252 may be delivered in a retrograde direction within a venous drainage structure of a target organ, and such retroperfusion may be phased to be performed during a non-flow period of cyclical venous drainage flow. For example, perfusion to the myocardium through perfusion port 252 may be performed during diastole, and may be ceased during systole. It is to be understood that such phasing perfusion may be performed in any of the embodiments of the present invention. The device of FIG. 12 does not include therapy deactivation by the blood conditioning apparatus, but nevertheless supplies perfusate at perfusion line 1 with conditioned blood, including, for example, being oxygenated and cooled. In this manner, perfusion line 1 may supply ischemic tissue with oxygenated and cooled blood for therapeutic treatment thereof. Without deactivation, the perfused therapy may affect systemic circulation over a period of time. However, such a system may be useful for relatively short duration, such as during PCI to re-establish vascularisation and arterial blood flow to an affected tissue structure.

Figure 11:
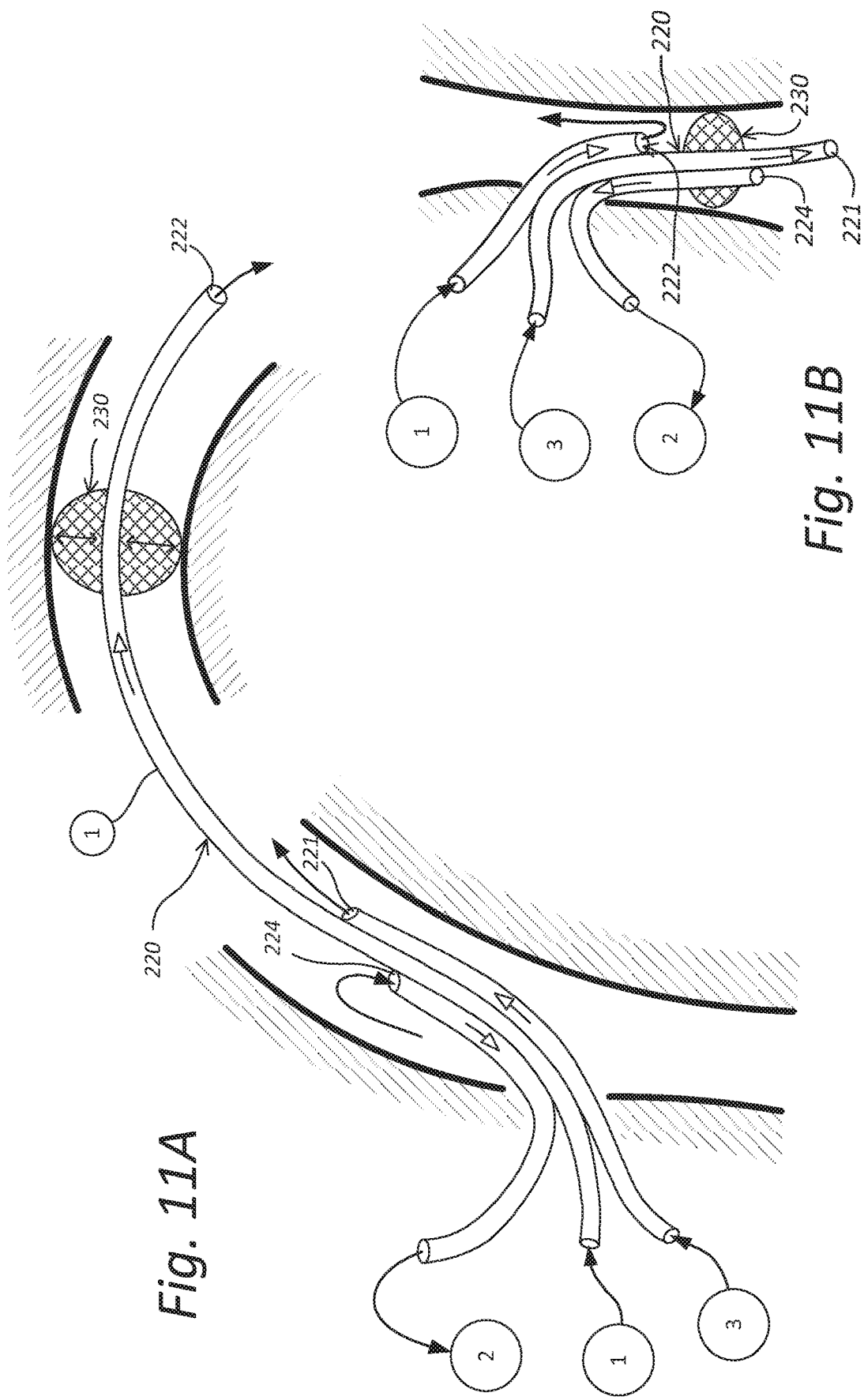
FIG. 11A is a schematic illustration of a therapy delivery system of the present invention.
FIG. 11B is a schematic illustration of a therapy delivery system of the present invention.

It is to be understood that the devices described in FIGS. 11 and 12 may be used in a variety of tissue structures/organs. An example application is delivery of the single-access catheter to the jugular vein to provide localized therapy to the intracranial venous sinuses. In such an embodiment, the perfusion port is disposed upstream from the deployed occlusion device, and perfusate may venously drain from the intracranial venous sinuses through another of the jugular veins. With the existence of collateral venous drainage, the occlusion device need not be cyclically inflated/deflated, and may instead be continuously deployed in an occlusive condition. The drainage port and systemic port for jugular vein access may be operably positioned in the systemic circulation where appropriate.

Any of the embodiments of the present invention may be employed as adjunctive therapy to, for example, an arterial intervention such as PCI for heart attack treatment. In the case of an adjunctive arterial intervention, an additional drainage line may be established to capture retrograde perfusate at the arterial side of the target tissue structure, and return at least a portion of the captured perfusate to the blood conditioning apparatus for reperfusion and/or dispensation to the systemic circulation. The additional drainage line may be incorporated with, for example, a stent delivery catheter or a thrombectomy catheter, so that arterial intervention with such catheters provides a convenient platform for also capturing perfusion flow from one or more separate venous catheters of the present invention. The additional drainage at the arterial side may be delivered to a blood conditioning apparatus of the present invention through a shunt or other line that is capable of drawing the reverse-flow drainage out from the additional drainage line. In some embodiments, an arterial suction pump may be employed to provide the necessary suction to draw the additional drainage to the blood conditioning apparatus. The suction effect may be enhanced with the use of an occlusion device in connection with the arterial drainage line, so as to substantially compartmentalize or separate the arterial circulation of the tissue structure from the systemic arterial circulation. The occlusion device may be operably disposed upstream from the arterial blockage, and may be operably positioned substantially upstream from the arterial blockage in order to minimize risk of inadvertent disruption of the blockage. Conventional thromboectomy catheters typically require positioning in close proximity to the arterial blockage, which can cause inadvertent breakage of the clot and/or plaque. Some thrombectomy catheters are even required to pass through the blockage in order to position a blood filter downstream of the blockage.

A unique benefit of this arrangement is to effectively inhibit clot and/or plaque debris from flowing downstream from the arterial intervention site. Instead, any debris is captured within the isolated organ circulatory compartment, and transferred to the blood conditioning apparatus for removal from the systemic circulation.

As indicated above, the catheters of the present invention may be equipped with various sensors, such as pressure, temperature, or chemical sensors, including direct organ electrical signal or electrogram sensors, to provide feedback control to ensure operating conditions within designated safety ranges. For example, pressure sensors may be disposed in the organ circulatory compartment to monitor the pressure therein, and therapeutic sensors, such as temperature sensors, chemical sensors, and the like, may be operably disposed at or near the drainage port for optimal feedback control.

One or more fixation mechanisms may be included with the catheters of the present invention to provide additional catheter stability, and to secure the catheter and occlusion device positions that are crucial for the isolation of the organ circulatory compartment. Such fixation mechanisms may be useful to prevent catheter dislodgement during, for example, programmed occlusion device deployment and collapse. Example fixation mechanisms are illustrated in FIGS. 13A and 13B. Fixation mechanisms 275, 277 may be expandable/retractable stents or coils. As illustrated in FIG. 13B, a pre-shaped coil-like catheter 280 may be stretched by a guide wire during catheter insertion and removal, and may be integrated in the catheter design. For multiple lumen catheters, only a single lumen may be pre-shaped, in the configuration illustrated in FIG. 13B.

Figure 14:
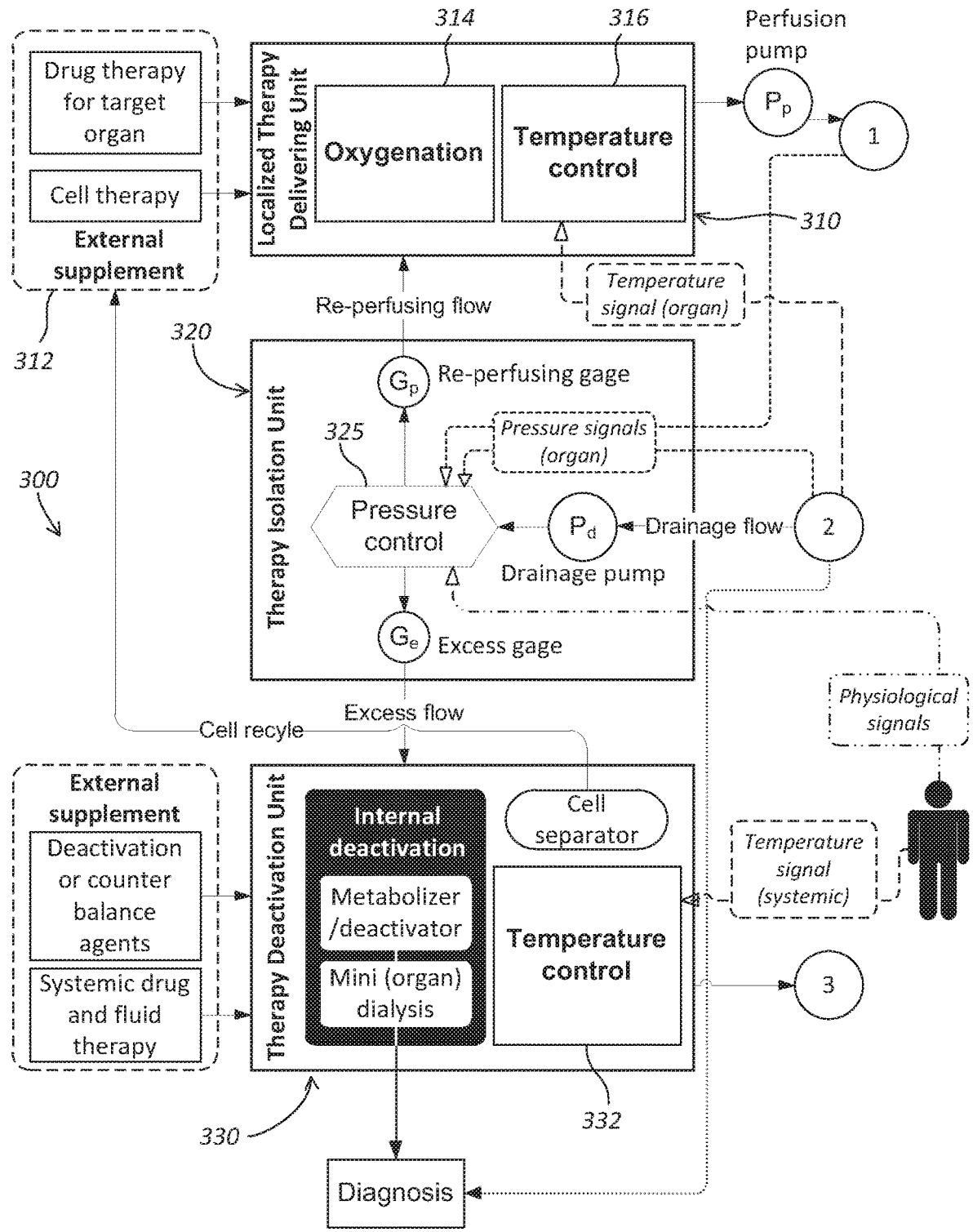
FIG. 14 is a schematic diagram of a therapy delivery system of the present invention.

The systems of the present invention are preferably adapted to deliver therapy to a target tissue structure through a perfusion line, localize the therapy to the specific target tissue structure, regulate the organ's circulatory flow volume, and deactivate the delivered therapy prior to re-entry to the systemic circulation through the systemic line. A schematic diagram of an extracorporeal blood conditioning apparatus of the present invention is illustrated in FIG. 14, wherein blood conditioning apparatus 300 includes a therapy delivery module 310, a therapy isolation module 320, and a therapy deactivation module 330. The schematic flow diagram of FIG. 14 illustrates example components of each module 310, 320, 330, and the fluid flow direction and connectivity, as well as example control pathways.

Localized therapy delivery provided by the present invention may include drugs, chemotherapy, cell or gene therapy, and/or physical treatment modality (e.g. therapeutic hypothermia). In addition, localized therapy delivery may include oxygenation in order to increase or ensure adequate oxygen supply of the target tissue structure. Therefore, therapy delivery module 310 may include one or more therapy delivery mechanisms including, for example, (i) external supplement 312 for supplemental drug or cell therapy, including chemotherapy or other supplements, (ii) oxygenation 314, and (iii) temperature control 316. External supplement 312 may include a flow control infusion pump (not shown) that may be synchronized to the perfusion flow 1, or independently controlled. Oxygenation 314 may be provided through a conventional membrane oxygenator or through the supply of hyperbaric aqueous oxygen, or combinations thereof. Temperature control 316, which may receive input signals from a temperature sensor within drainage line 2, provides therapeutic temperature to the target tissue structure. Such therapeutic temperature may include cooling for therapeutic hypothermia, or warming for countering the therapeutic hypothermia. As illustrated in FIG. 14, therapy delivery module is adapted to deliver perfusate to the venous access line (perfusion line 1).

Figure 15:
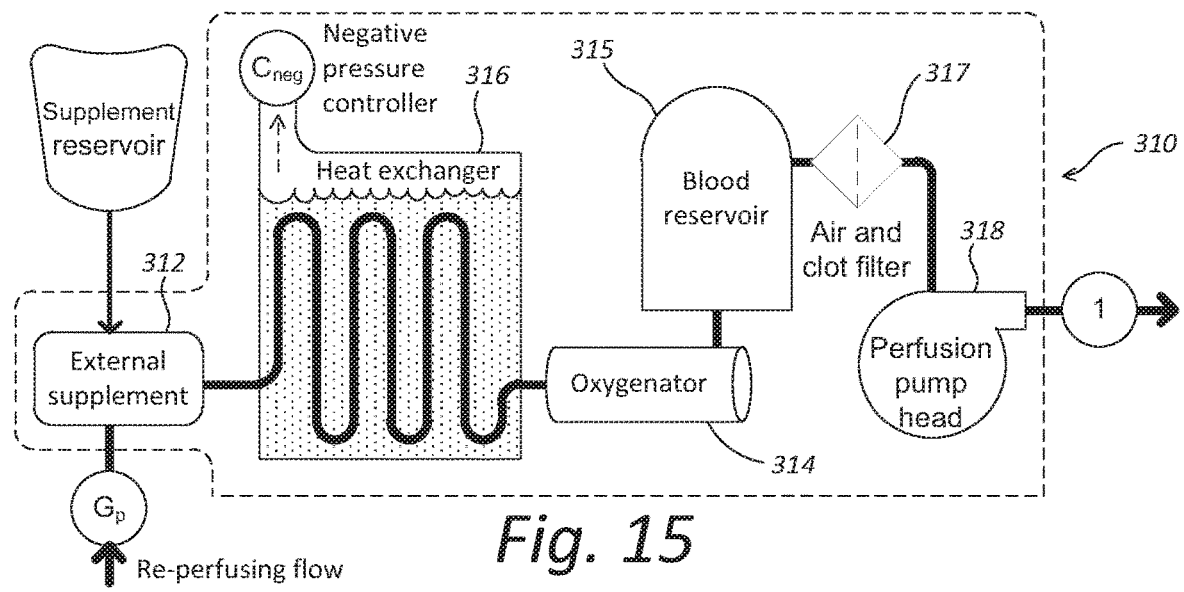
FIG. 15 is a schematic diagram of a portion of the system illustrated in FIG. 14.

A detailed exemplary flow diagram for therapy delivery module 310 is illustrated in FIG. 15. In the illustrated embodiment, therapy delivery module 310 includes a blood reservoir 315, an air/clot filter 317, and a perfusion pump 318 to drive the conditioned perfusate to the target tissue structure through perfusion line 1. In some embodiments, the components of therapy delivery module 310 are contained within a disposable blood circuit cartridge.

Therapy isolation module 320 is fluidly coupled to drainage line 2 of the catheter, and is adapted to control both the absolute and relative delivery and drainage of perfusate to and/or from the localized target tissue structure using the catheter in a manner that provides perfusate to substantially only the target tissue structure. In some embodiments, the drainage flow may exceed perfusion flow through perfusion line 1. In such embodiments, isolation unit 320 is responsible for maintaining optimal perfusion flow and safe intravascular or intravenous pressure within the target tissue structure. Therapy isolation module 320 therefore may be adapted to monitor flow volumes and intravascular pressure from the perfusion and drainage lines 1, 2, and diverting any excess flow to therapy deactivation module 330. As indicated in FIG. 14, drainage flow may be monitored and tested for diagnosis or disease progression monitoring, such as in monitoring cardiac enzymes for the diagnosis of heart attack.

Figure 16:
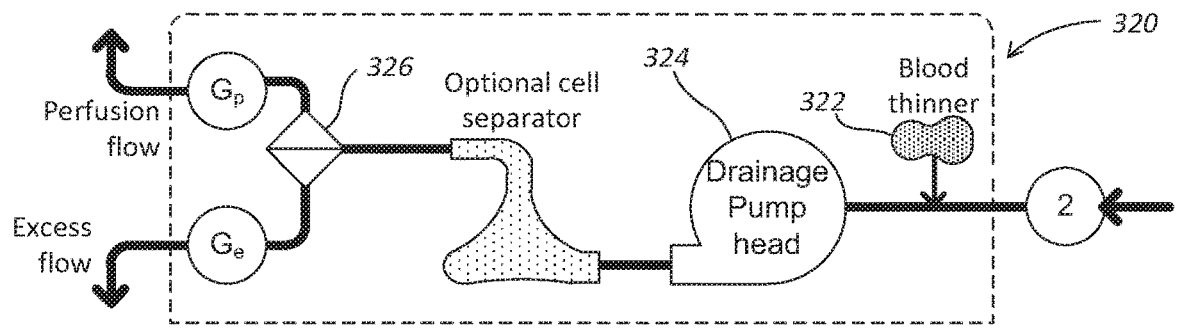
FIG. 16 is a schematic diagram of a portion of the system illustrated in FIG. 14.

An example flow diagram of therapeutic isolation module 320 is illustrated in FIG. 16. The embodiment of FIG. 16 includes a blood thinner addition mechanism to minimize clotting in the extracorporeal loop, a drainage pump 324, and a flow controller 326 for controlling division of flow and flow rate to each of therapy delivery module 310 and therapy deactivation module 330.

Where therapy isolation module 320 determines that drainage flow through drainage line 2 to be of a larger magnitude than the desired perfusion flow through perfusion line 1, a portion of the drainage flow is directed to therapy deactivation module 330 as excess flow. Before such excess flow is returned to the systemic circulation as systemic flow through systemic line 3, any remaining therapy agents or characteristics within the excess flow may be deactivated by therapy deactivation module 330 to prevent or minimize undesired systemic effects of such therapy agents or characteristics. The deactivation process depends upon the specific therapies delivered by therapy delivery module 310, and may be performed through internal deactivation and/or external deactivation.

Internal deactivation may include direct metabolizing (i.e. artificial liver) and dialysis (i.e. artificial kidney) for deactivation of therapeutic drugs and/or chemotherapy. The metabolizing methods employed may be specific to certain therapeutic agents, while the dialysis method may be more generally applied to a wide range of therapeutic agents. In the event that removal of the therapeutic agents through internal deactivation is insufficient, external deactivation may be applied through the addition of counter-balance antagonistic agents to the administered bioactive agents. Internal deactivation applies to removing one or more bioactive agents from the blood, while external deactivation supplies counteracting agents which interact with the systemic circulation. In some embodiments, the dialysate from the internal deactivation dialysis of therapy deactivation module 330 may be used for diagnosis or disease monitoring during the therapy administration. Moreover, systemic drug or fluid supplements may be administered through therapy deactivation module 330 as a convenient vascular access location.

Internal deactivation may further include a cell separator to reharvest cells used in cell-based therapy, and recycle the reharvested cells to therapy delivery module 310. Therapy deactivation module 330 may include a temperature control device 332 for modifying the temperature of the excess flow, such as to physiologic temperature for dispensation through systemic line 3. For therapeutic hypothermia applications, in which therapy delivery module 10 perfuses cooled perfusate to the target tissue structure, temperature control device 332 may be adapted to rewarm the excess flow to a physiologic temperature prior to return of the systemic flow to the systemic circulation. In this manner, the therapeutic hypothermia may be substantially isolated to the target tissue structure, while the remainder of the systemic circulation is substantially unaffected by such therapeutic hypothermia. The body or systemic temperature may therefore be independently controlled from the target tissue temperature. A feedback loop for the deactivating temperature control device 332 may be independent from the target tissue structure temperature control, such as by receiving body/systemic temperature signals from a sensor located within the systemic circulation.

Figure 17:
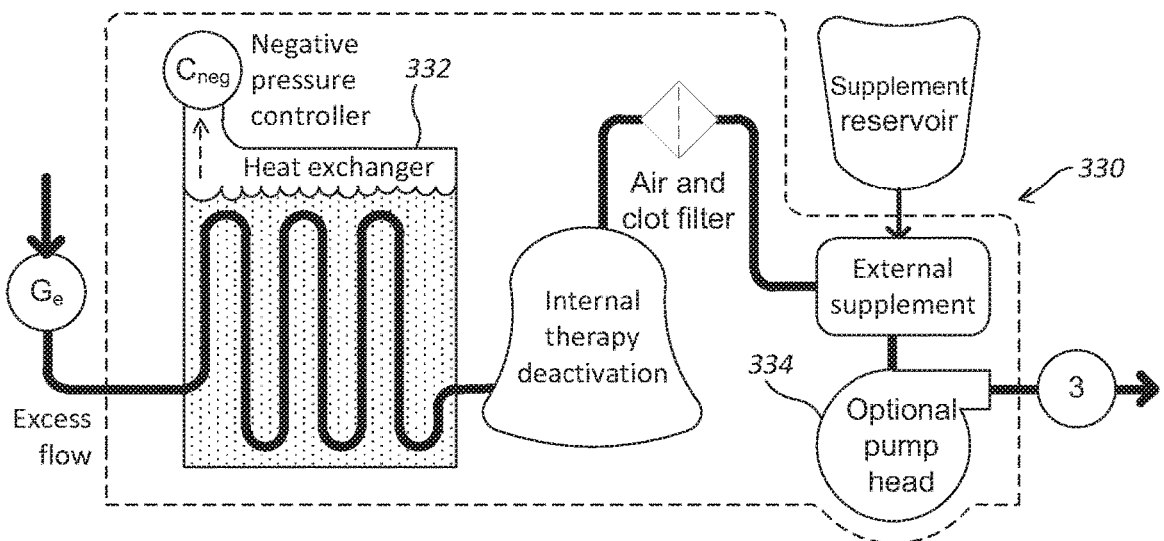
FIG. 17 is a schematic diagram of a portion of the system illustrated in FIG. 14.

A flow diagram of an exemplary therapy deactivation module 330 of the present invention is illustrated in FIG. 17. While the therapy deactivation module flow loop may be a passive flow, as driven by drainage pump 324, a systemic pump 334 may optionally be included to assist in flow direction control.

Though blood conditioning apparatus 300 is illustrated with a therapy deactivation module 330, it is to be understood that certain embodiments of the blood conditioning apparatus of the present invention need not include such therapy deactivation module 330. In particular, even without the therapy deactivation performed by therapy deactivation module 330, the target tissue structure/organ isolation obtained through the catheter arrangement of the present invention facilitates a relatively large organ-to-systemic concentration gradient. The localized therapy delivery may itself be considered a "passive" therapy deactivation, in that contamination of excess flow or collateral circulation is diluted by the large systemic blood volume, while at the same time the therapy concentration in the target tissue structure reaches a high therapeutic level.

Figure 18:
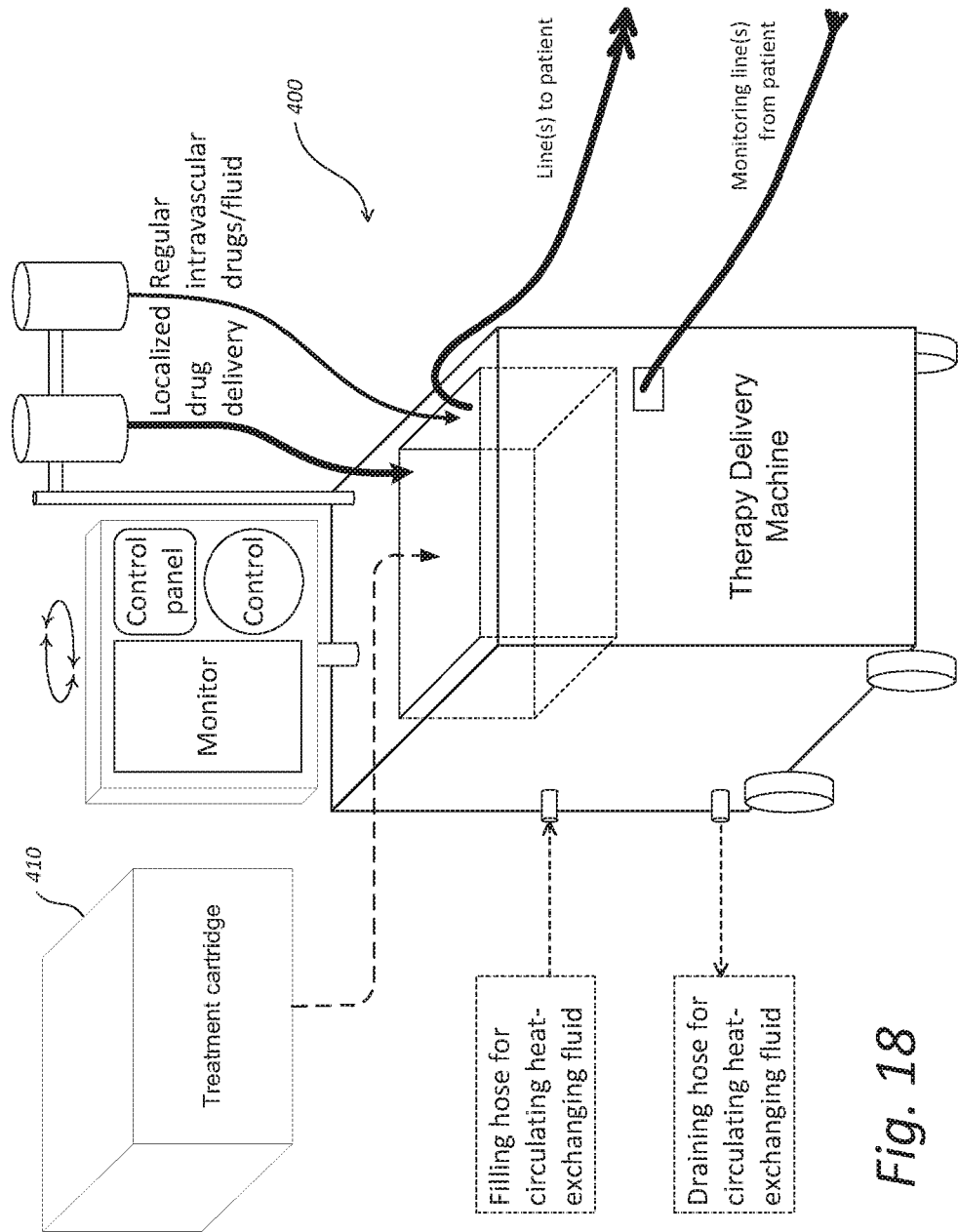
FIG. 18 is a schematic illustration of an implementation of the therapy delivery system of the present invention.

In one embodiment of the present invention, a delivery machine 400 may be provided to control the blood conditioning apparatus and the one or more catheters associated with the blood conditioning apparatus in order to deliver therapy to, and to drain some or all therapy from, the localized target tissue structure in a manner that provides therapy delivery to substantially only the localized target tissue structure. An example embodiment of delivery machine 400 is illustrated in FIG. 18, which is configured to connect and operate the therapy delivery module, the therapy isolation module, and the therapy deactivation module. Machine 400 may be arranged to facilitate blood conditioning and transfer without itself contacting the patient's blood. For example, while not contacting blood, machine 400 may include an oxygen supply unit, one or more temperature control units, non-contact blood pumps and flow-direction control, and internal deactivators.

Oxygen supply for oxygenating the perfusate may be supplied from a portable oxygen tank at machine 400, or a standard oxygen line from the facility, directly connected to an oxygenator 314 in therapy delivery module 310 within a treatment cartridge 410. In some embodiments, treatment cartridge 410 is operably engagable to machine 400, and may be the blood-contacting portion of the system, such that treatment cartridge 410 may be disposable. In place of, or in addition to the oxygen tank or facility oxygen line, machine 400 may include a hyperbaric aqueous oxygen solution mixing unit (not shown), which is adapted to inject oxygen-saturated saline to perfusion line 1.

The temperature control units 316, 332 may use distilled water as a heat exchanging media, with the heat exchangers disposed in treatment cartridge 410. Heating and cooling performed by temperature control units 316, 332 may be performed by a thermal-electric device which may be controllably switched between heating or cooling by alternating the electrical current. Confined in the tubing in cartridge 410 to prevent contamination with machine 400, the blood flow may be driven by a rolling or peristaltic pump on machine 400. Such pump may also control blood flow direction.

Figure 19A:
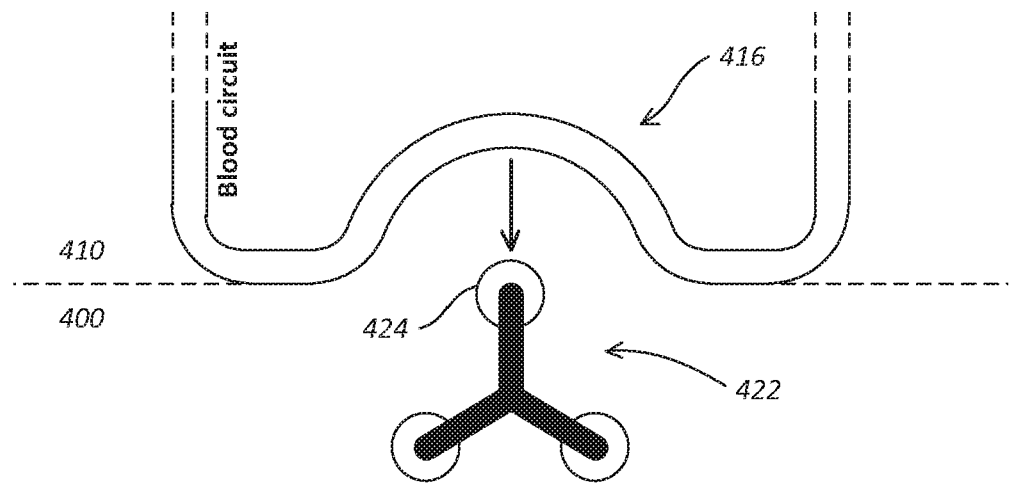
FIG. 19A is a schematic illustration of a portion of the system illustrated in FIG. 18.
Figure 19B:
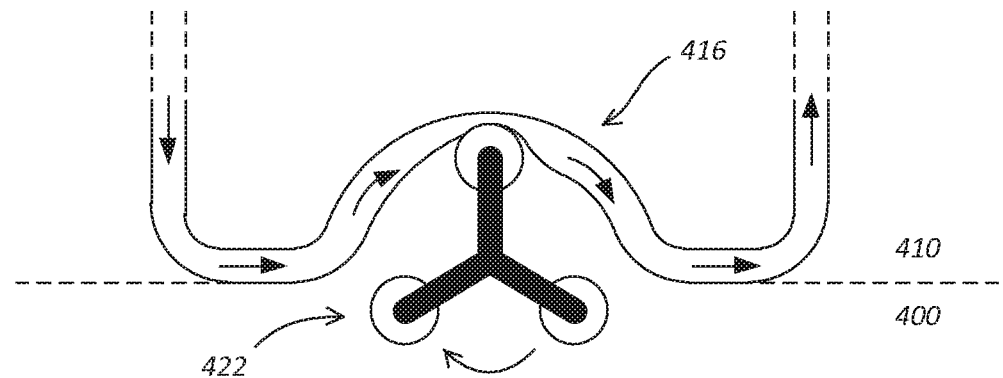
FIG. 19B is a schematic illustration of a portion of the system illustrated in FIG. 18.

As indicated above, treatment cartridge 410 may include one or more of therapy delivery module 310, therapy isolation module 320, and therapy deactivation module 330. In one embodiment, treatment cartridge 410 includes each of modules 310, 320, 330. Cartridge 410, therefore, embodies functionality that may be carried through the facilities of machine 400. Machine 400 may be specifically configured to operably receive treatment cartridge 410 in a quick-connect/disconnect manner, with connections for, e.g., oxygenation, temperature control, fluid pumping, and therapy deactivation connections may be automatically established upon fitment of treatment cartridge 410 into operating engagement with machine 400. FIGS. 19 and 20 illustrate example self-engaging mechanisms for pump heads 416, 418 of treatment cartridge 410 to be operably engagable with rolling pump 422 of machine 400. FIG. 19A illustrates cartridge 410 prior to operable engagement with machine 400, while FIG. 19B illustrates the interaction between rolling pump 422 of machine 400 with pump head 416 of cartridge 410 subsequent to operable engagement of cartridge 410 to machine 400. In a particular embodiment, operable engagement may include physical engagement of cartridge 410 to a receptacle of machine 400.

Figure 20A:
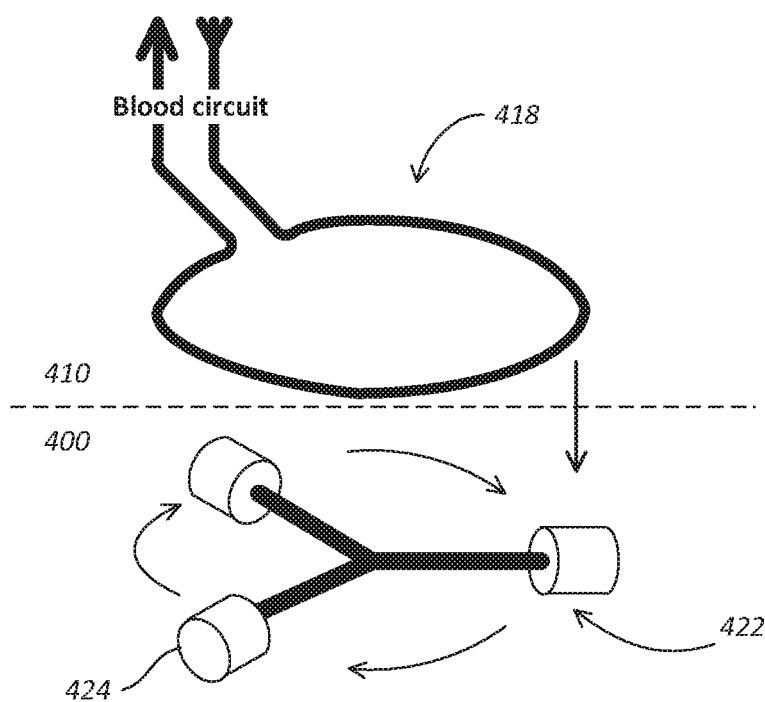
FIG. 20A is a schematic illustration of a portion of the system illustrated in FIG. 18.
Figure 20B:
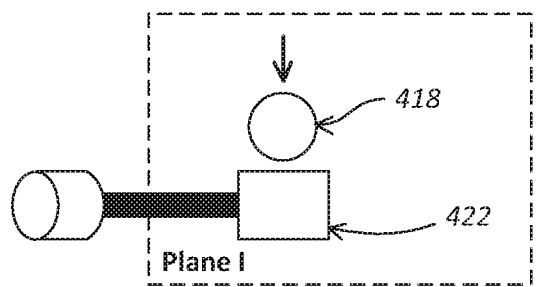
FIG. 20B is a schematic illustration of a portion of the system illustrated in FIG. 18.
Figure 20C:
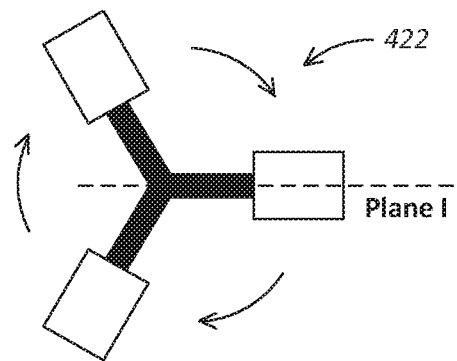
FIG. 20C is a schematic illustration of a portion of the system illustrated in FIG. 18.

An alternative example arrangement is illustrated in FIGS. 20A-20C, in which pump head 418, which may be a blood circuit within disposable tubing, may be operably engaged with rolling pump 422 of machine 400 in a top-down approach. In each of the embodiments illustrated in FIGS. 19 and 20, rollers 424 of rolling pump 422 operably engage pump head 416, 418 to cause flow of fluid through the blood circuit.

The temperature control devices of cartridge 410 may incorporate negative pressure induced in the heat exchanger compartment to avoid contamination from the heat exchanging fluid into the blood flow. In case of a leak on the heat exchanger loop, blood flow is drawn to the heat exchanger compartment, rather than vice versa. A hemoglobin detector may also be equipped in the heat exchanger compartment to monitor any potential leaks. In any event, abrupt pressure changes in both the heat exchanger and blood flow compartments may be used as an indication for system leakage.

External supplement devices may connect directly to cartridge 410, which cartridge 410 may connect directly to the catheters of the present invention. In the event that a cell separator device is included, cartridge 410 may employ a line transferring the cells to therapy delivery module 310 from the cell separator in the therapy deactivation module. In the event that therapy deactivation module 330 includes a metabolizer or dialyzer, cartridge 410 may include an exhaust line for the metabolite dialysate.

Figure 21:
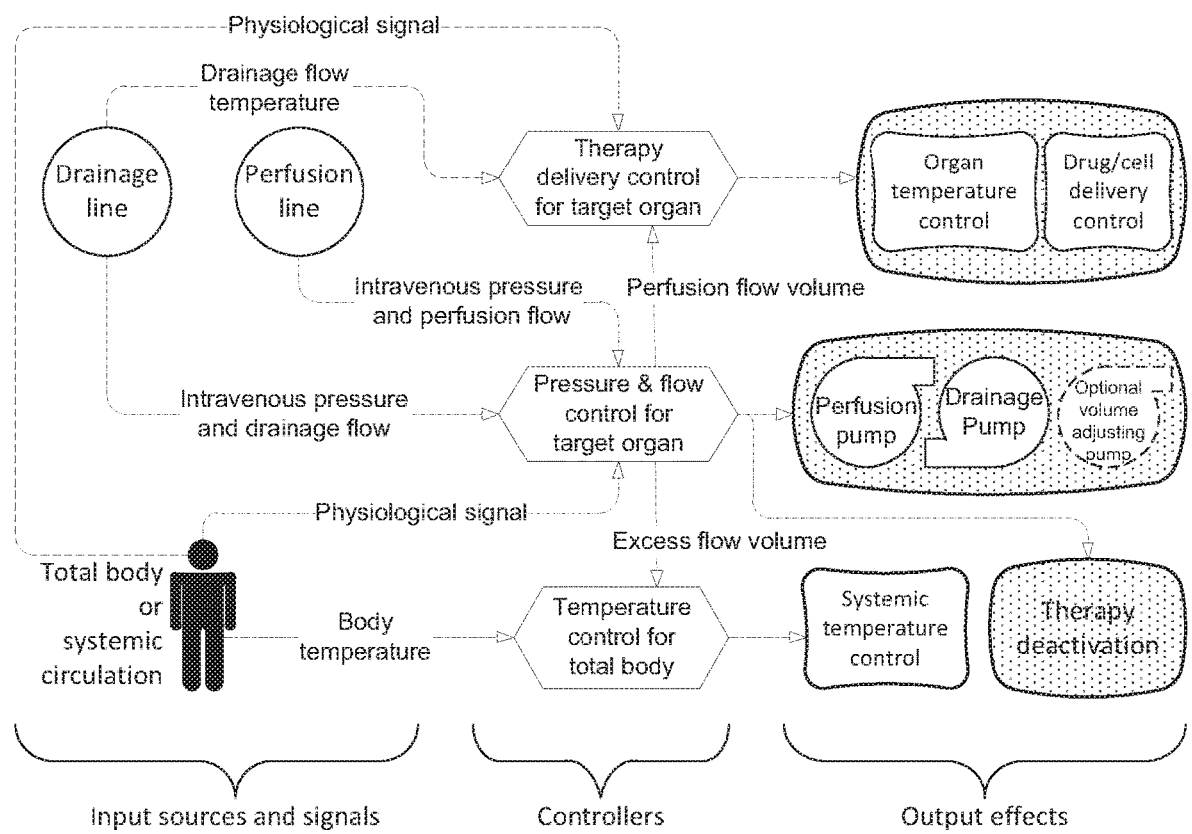
FIG. 21 is a schematic flow diagram of a portion of the therapy delivery system of the present invention.

An example control circuit summary for a blood conditioning apparatus of the present invention is illustrated in FIG. 21. Pressure from both perfusion line 1 and drainage line 2 may be monitored to determine intravenous pressure of the target organ. Target organ pressure information may be delivered to a pressure control unit in therapy isolation module 320, along with other appropriate physiologic signals to control perfusion flow and drainage flow. Pressure control unit 325 may act as a flow divider that is responsive to control signals delivered from sensors which sense pressure at, for example, the perfusion port, so as to adjust the division of drainage flow among the perfusion flow and the systemic flow. Sensors may be deployed to detect not only intravenous pressure, but also a variety of characteristics, and to communicate signals representative of values of such characteristics to pressure control device 325 of the blood conditioning apparatus. The sensors may be adapted to detect characteristics, such as pressure, temperature, flow rate, electrogram signal, enzyme concentration, and therapeutic drug concentration.

Perfusion and drainage pumps 318, 324 may control flow rates, flow direction, and timing to provide synchronized flow patterns to the various target tissue structures/organs. By receiving flow information from perfusion line 1 and drainage line 2, pressure/flow control device 325 is able to adjust deactivation therapy according to the volume of excess flow delivered to therapy deactivation module 330. Data on perfusion and excess flow volume may also be delivered to temperature control devices 316, 332 to optimize temperature adjustment of perfusate and systemic flow.

In some embodiments, temperature control device 316 receives temperature information from a temperature sensor disposed in drainage line 2. Such a temperature signal may be used as a feedback for localized therapeutic hypothermia at the target tissue structure to monitor temperature thereat. Moreover, confirmatory information regarding target tissue temperature in a therapeutic hypothermia application may also be obtained by physiological signals, such as electrograms, including an electrocardiogram from the myocardium. Temperature feedback information may be utilized to estimate therapy delivery or concentration in the target tissue structure. Such information may also be useful for localized therapy delivery for bioactive agents which are difficult to remotely sense. A further temperature control may include a systemic or total body temperature sensing, such that the excess flow may be used to regulate the body temperature, and to maintain a desired organ to systemic temperature gradient. In such a manner, target organ temperature may be maintained within a therapeutic range, while maintaining a desired (e.g. normal) body temperature.

Example Applications

The following sets forth example clinical applications of the system of the present invention. The applications described herein are not intended to be limiting to the various applications contemplated by the present invention.
Isolated Organ-Specific Therapeutic Hypothermia Therapeutic hypothermia is a treatment using mild hypothermia (32° C. to 34° C.) to prevent or minimize reperfusion injury. The treatment has shown to provide significant benefits for both ischemic and traumatic injuries for many organs (e.g. heart, brain, liver, and kidney, etc.) The goal of using this isolated organ-specific therapy delivery is to localize the cooling therapy to a specific target organ, while maintaining normal body temperature. This will enable the use of therapeutic hypothermia for conscious patients (i.e. without medically-induced coma and strong muscle relaxant), and prevent systemic side effects of the cooling treatment.

Since the indication of use for therapeutic hypothermia is mostly for emergency circumstances, timely implementation and ease of use is an important factor in the design of a therapy delivery device. Therefore, a system requiring only venous access is most preferred. Selection between one-vein access and two-vein access techniques depends on the target organ. In applying therapeutic hypothermia to the heart, the one-vein access may be a better choice because of the coronary sinus being a major venous drainage of the ventricular muscle, and its easy access and well-established procedure. For application to the brain, the two (left and right) internal jugular veins make the two-vein access technique a possible candidate. Nevertheless, the complete isolation organ-circulation techniques described herein can also be used for therapeutic hypothermia.

For the device setting of therapeutic hypothermia, there is not much change on the therapy delivery and isolation parts from the general description. For solely cooling treatment, there is no need for the external supplemental unit. However, small amount of drugs (i.e. a beta blocker to control heart rate and myocardial contractility, anti-arrhythmia or anti-convulsion drugs, and/or magnesium sulfate for both heart attack and stroke) can also be administrated locally to the target organ with hypothermia treatment. The target organ may have the additional benefit of increased oxygenation from the organ isolation technique as well. The only required component for the deactivation part is the systemic temperature control.

The function of the target organs (i.e. particularly for the heart—acute myocardial infarction, and the brain—stroke) may be preserved while the localized delivery technique is employed. There are two major impacts of these novel localized delivery methods for standard heart attack and stroke treatment. One is organ cooling prior to reperfusion. For the first time, the heart or the brain or other target organs may be cooled to the therapeutic temperature in only a few minutes (typically within 15 minutes). This allows for cooling before an establishment of the local reperfusion (balloon/stent or thrombolytic angioplasty), which is known to provided the best cell protection. Secondly, extended cooling treatment (e.g. 12 to 72 hours) is possible for awake patients. This maximizes the cell salvaging benefit of mild hypothermia. For cardiac arrest, a local brain cooling can be used without medically-induced coma. Therefore, a time period exceeding 24 hours of mild hypothermia can be used. Neurological signs of cardiac-arrest patients' can be monitored while the cooling treatment is being employed, which may be used to individually optimize the length of therapeutic hypothermia.

Isolated Organ-Specific Drug & Chemotherapy

Many drugs require a high therapeutic dosage at the target organ to be effective, which cause severe systemic side effects. Chemotherapy is an example of a highly toxic bioactive agent. Many cancer patients die from complications of the chemotherapy rather than from the cancer. That limits the use of chemotherapy for many patients. The isolated organ therapy delivery technique can also be used to deliver drugs that require high organ-to-systemic concentration gradient. The goal is to maintain the high concentration in the target organ, but keep a very low concentration in the systemic circulation. Chemotherapy is a good candidate for this localized therapy delivery, as its administration usually takes several hours to few days. The organ isolation can also be maintained for additional days thereafter.

Since this type of application is usually employed in scheduled visits, the choice of the organ isolation technique is more open and depends on the target organ or organ segment or tumor vasculature. For example, a two-vein access partial isolation technique may be an optimal choice for brain. For the liver, however, both 2-vein and 1-vein access partial isolation techniques may be suitable, depending on the desired location and extent of circulatory isolation within the liver. One-access partial organ circulatory isolation may be a good candidate for the renal vein of the kidney. In addition, a complete isolation technique can also be very useful if the risk of local and systemic arterial embolization can be managed. For cancer masses, the eligibility or choices of the organ-circulatory isolation technique purely depends on the vascular structure.

Therapeutic agents may be added to the perfusion line to deliver localized therapy to the target organ. Although there may be no need for altering organ temperature, a small warmed or cooled saline may be injected in the perfusion line and the temperature sensing on the drainage line may be able to calculate effectiveness of the therapy delivery. The feasibility of this technique depends on the vascular architecture of the target organ and the arrangement of the isolation technique.

If available, antidotes for drugs can be used to deactivate or neutralize the therapy delivery. Mini organ dialysis may also be used to excrete some drugs or therapeutic agent from the blood volume returning to the systemic circulation. Nevertheless, localized delivery and isolation of the therapy alone without the deactivation may be able to raise the concentration of the therapeutic agents in or at the target organ to a sufficient extent, while contamination to the system may be diluted to a more tolerable level for the patients. Because of the relatively small volume of the target organ (compared to the total body), a relatively small amount of drugs are likely needed in a localized therapy delivery approach, which also reduces treatment costs for expensive drugs like chemotherapy. Since systemic side effects may be minimized by the localized delivery method of the present invention, existing chemotherapy protocols may be revised for longer administration periods and higher dosages for the local organ.

Isolated Organ Protection

Conventional administration of toxic bioactive agent therapy is through systemic treatment. However, the therapeutic bioactive agent may have toxicity to certain vital organs—such as liver, kidney, or heart. In addition to providing localized therapy delivery, the organ-circulatory isolation technique of the present invention can also be used to protect the target organ from a systemic treatment by creating a high systemic-to-organ concentration gradient. Therefore, the organ circulation is isolated or separated from the system circulation.

In this application, complete organ-circulatory isolation may be the most effective, as it prevents or significantly reduces incoming blood flow from the arterial system. Nevertheless, the partial isolation techniques described herein are also useful in diluting and neutralizing the toxicity from the incoming arterial flow. The vasculature of the target organ is the most dominant factor in selecting the organ-circulatory isolation technique. For example, the presently described partial isolation technique may be a better choice for the liver, while the kidney may be a good candidate for either of the complete and partial isolation techniques.

Figure 22:
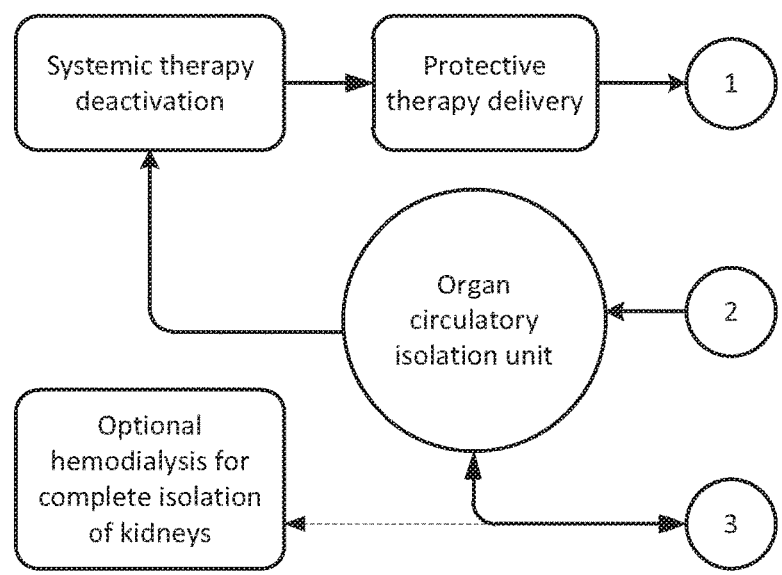
FIG. 22 is a schematic flow diagram of a portion of the therapy delivery system of the present invention.

To accommodate this application, the therapy deactivation module may instead be on the perfusion side, as shown in FIG. 22. However, the oxygenation and the temperature control units may remain on the (protective) therapy delivering module. The goal of this application is to deactivate or neutralize the therapy. In case of the need to protect both kidneys with the complete isolation technique of the present invention, a temporary hemodialysis through flow-volume adjusting line may be required as the kidney's dialysis function is shielded from the systemic blood circulation.

Isolated Organ-Specific Cell-Based Therapy

Stem cell therapy or regenerative medicine is in development, and may soon become a common therapy modality. One of the many challenges facing cell therapy is low cell seeding or survival rate. Cells are traditionally delivered through an arterial line such that a majority of delivered cells pass through the capillary or collateral circulation too quickly, and do not have enough time to seed into the tissue bed. Delivering these cells through the venous system may help increase contact time with the tissue bed. Moreover, the organ-circulatory isolation of the present invention may recycle cells to the target organ. Therefore, the organ isolation techniques can be used to improve seeding rate for cell-based therapy. Because of the smaller volume of an organ (vs. the volume of the total body), a relatively smaller number of cells may be needed to promote cell based therapy in the system of the present invention, as compared to conventional systemic administrations.

Figure 23:
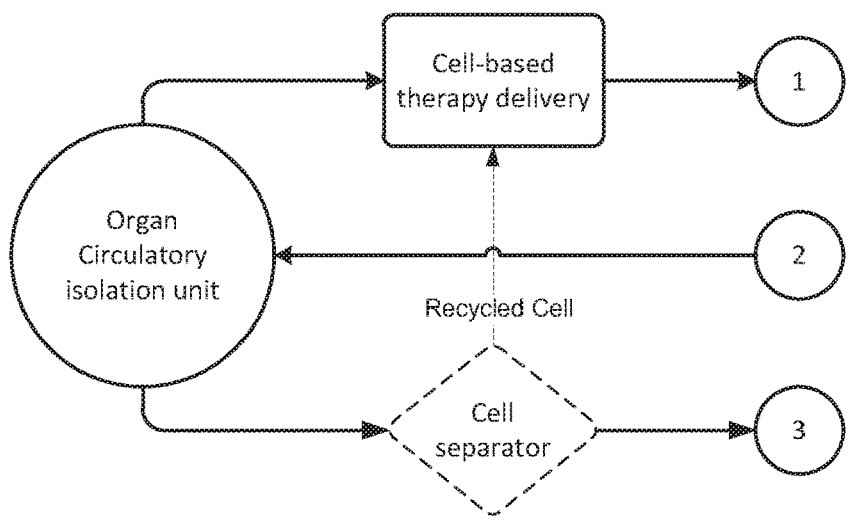
FIG. 23 is a schematic flow diagram of a portion of the therapy delivery system of the present invention.

Partial organ-circulatory isolation techniques may be first considered to avoid prolonged arterial access during the localized therapy delivery. The choice of one-vein access or two-vein access depends on vascular architecture of the target organ—in the same manner discussed in previous applications. The device setting may require a cell separator to recycle cells back to the target organ, as shown in FIG. 23. However this may not be a crucial component if the supply for the cell therapy is not too limited. This application may not need other deactivation components.

Figure 24:
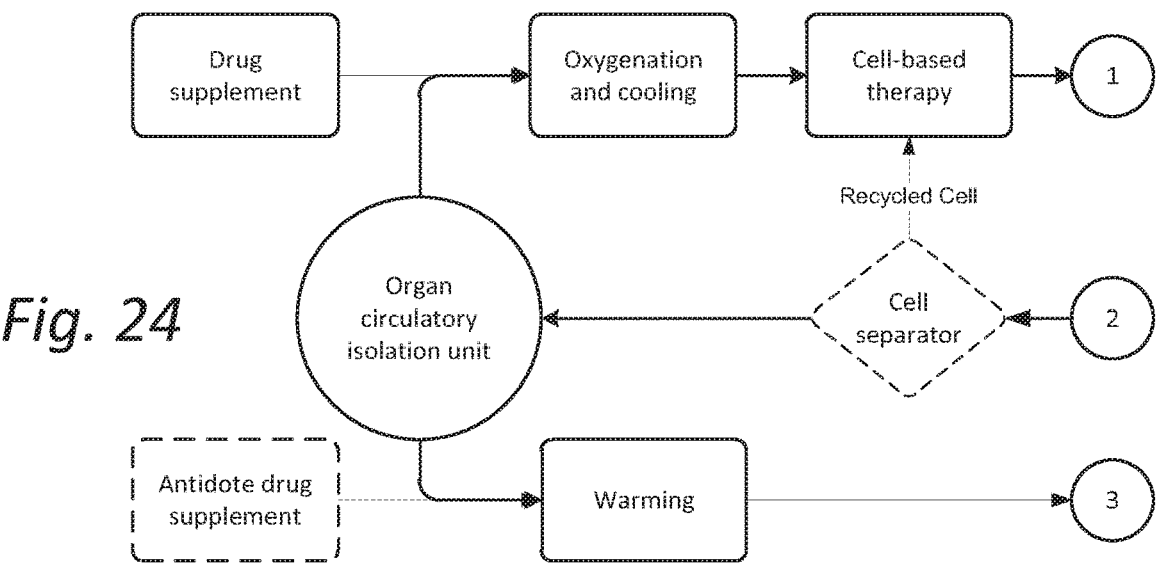
FIG. 24 is a schematic flow diagram of a portion of the therapy delivery system of the present invention.

Examples of this application may include cell-based therapy for chronic myocardial infarction, chronic liver failure, and chronic renal failure. Stem cells may be injected through these diseased organs to permanently reinstall the failed organ function. This can also be combined with mild cooling, shown FIG. 24, which has been shown to improve cell survival rate.

Isolated Organ-Specific Plasma Paresis and Dialysis

In events of large organ injury where toxicity secondary to the injury can cause a severe insult to the entire body, this organ isolation method can be used to separate the organ from the systemic circulation prior to performing plasma paresis and/or dialysis to remove the toxicity produced by the injured cells. By doing so, localized treatment can also be employed to help cell recovery and also to protect the organ from reperfusion injury. One example of this application is to isolate an extremity (i.e. arm or leg) in which the blood supply has been cut for more than several hours. This is usually an indication for amputation to prevent reperfusion injury to the whole body that could cause severe complications, such as acute renal failure or heart failure, or even death. Another example application is gangrene of large internal organs.

Figure 25:
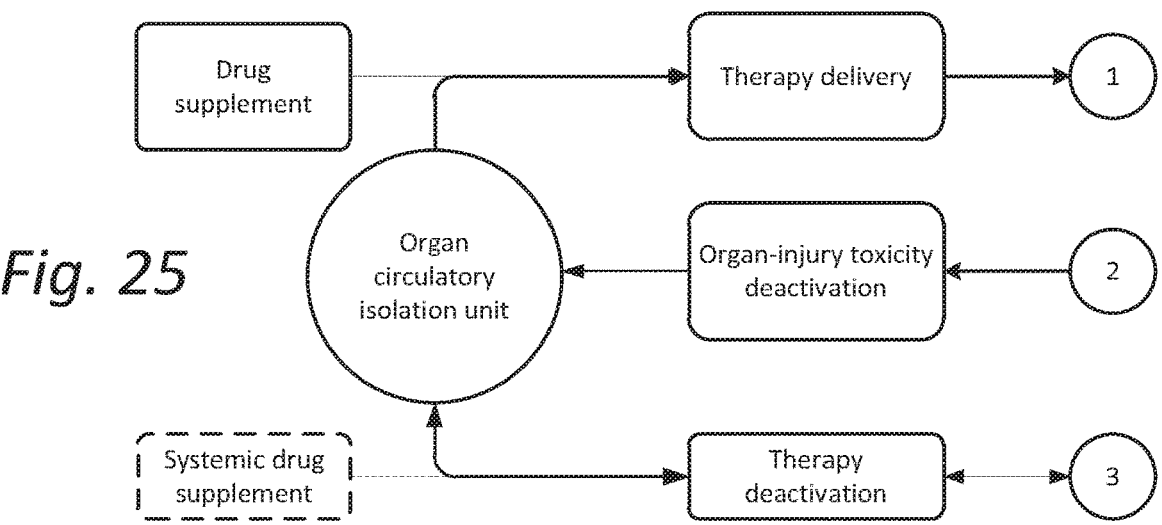
FIG. 25 is a schematic flow diagram of a portion of the therapy delivery system of the present invention.

Since this application is primarily for large volume organs, the complete organ isolation technique of the present invention may be an appropriate choice. For arms and legs, the vascular access for both arterial and venous systems is easily obtained through the brachial or axial arteries and veins, and the femoral arteries and veins. The device setup may be as shown in FIG. 25, wherein the toxicity deactivation unit may be adapted to treat the drainage flow. Oxygenation and mild cooling may be included to provide tissue oxygen supply and to prevent additional reperfusion damage to injured tissue.

This itself is a treatment, rather than just a therapy delivery, that could help preserve arms or legs which otherwise would be amputated. This can help reduce disability which is extremely expensive not only to the healthcare system but to the society as a whole—and more importantly help improve or preserve patients' quality of life.

What is claimed is:

1. A system for perfusing a localized site within a body, the system comprising:
   (a) a catheter apparatus comprising:
      (i) a venous access line adapted to deliver perfusate to the localized site;
      (ii) a venous drainage line adapted to recover drainage flow from the localized site; and
      (iii) an occlusion device adapted to selectively block venous blood flow between the localized site and systemic circulation of the body;
   (b) a blood circuit associated with the catheter apparatus to facilitate blood conditioning for use as the perfusate in the course of a controlled perfusion and drainage of blood to and from the localized site, the circuit comprising:
      (i) a therapy delivery module adapted to deliver perfusate to the venous access line; and
      (ii) a therapy deactivation module for optionally deactivating at least a portion of the drainage flow, wherein the deactivating includes one or more of warming the drainage flow, metabolizing a bioactive agent in the drainage flow, and counteracting the bioactive agent in the drainage flow; and
   (c) a delivery machine adapted to control the blood circuit and catheter apparatus in order to both deliver perfusate to, and recover drainage flow from the localized site in a manner that provides perfusate to substantially only the localized site.

2. A system as in claim 1 wherein the occlusion device is an inflatable balloon.

3. A system as in claim 2 wherein the venous access line comprises a catheter having proximal and distal ends, the proximal end being connected in fluid communication with the blood circuit, the distal end being substantially open to the flow of the blood into and/or from the catheter, and the inflatable balloon being positioned between the proximal and distal ends in order to occlude blood flow between the localized site and the systemic circulation.

4. A system as in claim 1 wherein the perfusate comprises autologous blood that has been conditioned in a manner selected from the group consisting of:
   (a) the addition of one or more bioactive agents;
   (b) the removal of one or more bioactive agents from the blood; and
   (c) the physiological modification of the blood in order to promote a corresponding response in the localized site.

5. A system as in claim 4 wherein the localized site is selected from the group consisting of heart, brain, liver, kidney, arm, and leg of a patient.

6. A system as in claim 1 wherein the catheter apparatus includes a venous volume adjustment line adapted to fluidically connect the blood circuit with the systemic circulation.

7. A system as in claim 6 wherein flow may be driven bi-directionally through the venous volume adjustment line.

8. A system as in claim 1 wherein the delivery machine is adapted to apply a suction force to the venous drainage line.

9. A system for delivering localized therapy to a tissue structure, said system comprising:
   a catheter apparatus including:
      (i) a first venous catheter having a distal portion positionable at a first venous structure of said tissue structure, said distal portion including an occlusion device adapted to selectively substantially occlude said first venous structure to define a tissue structure circulatory compartment and a systemic circulatory compartment, said first venous catheter including a perfusion port positionable in said tissue structure circulatory compartment;
      (ii) a second venous catheter having a drainage port positionable in said tissue structure circulatory compartment;
      (iii) a systemic port associated with one of said first and second venous catheters, the systemic port being positionable in the systemic circulatory compartment;
   a blood conditioning apparatus fluidly coupling said perfusion port, said drainage port, and said systemic port, said blood conditioning apparatus being capable of conditioning blood supplied thereto as drainage flow through said drainage port, and dispensing at least one of: (a) conditioned perfusion flow through said perfusion port; and (b) systemic flow through said systemic port.

10. A system as in claim 9, including a venous volume adjustment line fluidically connecting the blood conditioning apparatus to the systemic port, wherein the blood conditioning apparatus is adapted to drive blood flow bi-directionally to and from the systemic circulatory compartment through the venous volume adjustment line.

11. A system as in claim 9 wherein the first venous structure is a first jugular vein, and the second venous catheter is positionable in a second jugular vein, and wherein the tissue structure is a brain.

12. A system as in claim 11, including a second occlusion device adapted to selectively occlude the second jugular vein.

13. A method for localized therapy of a tissue structure, said method comprising:
   (a) providing a catheter apparatus having:
      (i) a perfusion line for conveying perfusion flow to the tissue structure;

(ii) a drainage line for recovering drainage flow from the tissue structure, the drainage line and the perfusion line together forming an organ circulation loop;
(iii) a systemic access line having a systemic port; and
(iv) an occlusion device;
(b) providing a blood conditioning apparatus associated with said catheter apparatus for:
(i) controlled perfusion to the tissue structure;
(ii) controlled flow through the systemic access line; and
(iii) conditioning of the drainage flow;
(c) positioning said catheter apparatus within a drainage outlet of the tissue structure;
(d) actuating said occlusion device to selectively occlude drainage from the tissue structure, and to thereby define a tissue structure circulatory compartment and a systemic circulatory compartment, wherein the systemic port is positioned in the systemic circulatory compartment;
(e) receiving the drainage flow to the blood conditioning apparatus from the drainage line;
(f) selectively driving flow to and from the organ circulation loop through the systemic port;
(g) conditioning blood flow from a blood source to generate at least one of the perfusion flow and a systemic flow, wherein the blood source includes the drainage flow; and
(h) dispensing the perfusion flow to the tissue structure circulatory compartment through said perfusion line.

14. A method as in claim 13 wherein the perfusion line includes a perfusion port positioned in the tissue structure circulatory compartment, and the drainage line includes a drainage port positioned in the tissue structure circulatory compartment.

15. A method as in claim 14 wherein the conditioning includes cooling the blood flow to less than 35° C.

16. A method as in claim 15 wherein the cooled blood flow is the perfusion flow.

17. A method as in claim 13, including positioning the perfusion line within a first jugular vein, and positioning the drainage line within a second jugular vein.

18. A method as in claim 17 wherein the tissue structure is a brain.

19. A method as in claim 13 wherein the conditioning includes deactivating the blood flow, wherein the deactivating includes one or more of warming the drainage flow, metabolizing a bioactive agent in the drainage flow, counteracting the bioactive agent in the drainage flow, and removing the bioactive agent from the drainage flow.

20. A method as in claim 13, including withdrawing the drainage flow from the tissue structure circulatory component by applying a reduced pressure within the drainage line.

* * * * *